United States Patent
Barrett et al.

(10) Patent No.: US 11,365,389 B2
(45) Date of Patent: *Jun. 21, 2022

(54) CELL CULTURE MEDIUM COMPRISING SMALL PEPTIDES

(71) Applicant: Life TECHNOLOGIES CORPORATION, Carlsbad, CA (US)

(72) Inventors: Shawn Barrett, Norfolk, MA (US); Scott Jacobia, East Amherst, NY (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,242

(22) Filed: Jun. 16, 2020

(65) Prior Publication Data

US 2020/0308537 A1  Oct. 1, 2020

Related U.S. Application Data

(60) Continuation of application No. 15/349,791, filed on Nov. 11, 2016, now Pat. No. 10,793,827, which is a division of application No. 13/092,016, filed on Apr. 21, 2011, now abandoned.

(60) Provisional application No. 61/327,644, filed on Apr. 23, 2010.

(51) Int. Cl.
*C12P 21/02* (2006.01)
*C12N 5/00* (2006.01)

(52) U.S. Cl.
CPC .......... *C12N 5/0018* (2013.01); *C12N 5/005* (2013.01); *C12P 21/02* (2013.01); *C12N 2500/32* (2013.01); *C12N 2501/998* (2013.01); *C12N 2510/02* (2013.01)

(58) Field of Classification Search
CPC  C12N 5/0018; C12N 5/005; C12N 2501/998; C12N 2510/02; C12N 2500/32; C07K 5/06; C12P 21/02
See application file for complete search history.

(56) References Cited

U.S. PATENT DOCUMENTS

| | | | |
|---|---|---|---|
| 4,235,772 | A | 11/1980 | Bergendal et al. |
| 4,968,696 | A | 11/1990 | Stehle et al. |
| 5,122,469 | A | 6/1992 | Mather et al. |
| 5,206,220 | A | 4/1993 | Hilton |
| 5,328,844 | A | 7/1994 | Moore |
| 5,534,538 | A | 7/1996 | Drauz et al. |
| 5,543,397 | A | 8/1996 | Drauz et al. |
| 8,252,557 | B2 | 8/2012 | Katayama et al. |
| 10,793,827 | B2 * | 10/2020 | Barrett ............. C12N 5/0018 |
| 2002/0142966 | A1 | 10/2002 | Bair et al. |
| 2003/0130195 | A1 | 7/2003 | Amiot |
| 2005/0143296 | A1 | 6/2005 | Tsubouchi et al. |
| 2006/0051861 | A1 | 3/2006 | Primiano |
| 2011/0212489 | A1 | 9/2011 | Gadellaa et al. |

FOREIGN PATENT DOCUMENTS

| | | |
|---|---|---|
| AU | 2011242496 C1 | 3/2017 |
| DE | 202011110859 U1 | 12/2016 |
| EP | 0087750 A2 | 9/1983 |
| EP | 0087751 A2 | 9/1983 |
| EP | 0087750 B2 | 4/1994 |
| EP | 2154244 A1 | 2/2010 |
| EP | 2351833 A1 | 8/2011 |
| EP | 2610338 A1 | 7/2013 |
| EP | 2561065 B1 | 11/2016 |
| GB | 2251249 A | 7/1992 |
| JP | 2009102488 A | 5/2009 |
| JP | 6016783 B2 | 10/2016 |
| WO | WO-8700195 A1 | 1/1987 |
| WO | WO-8803150 A2 | 5/1988 |
| WO | WO-9116067 A1 | 10/1991 |
| WO | WO-9626266 A1 | 8/1996 |
| WO | WO-0202591 A2 | 1/2002 |
| WO | WO-03046141 A2 | 6/2003 |
| WO | WO-03085138 A1 | 10/2003 |
| WO | WO-2006075486 A1 | 7/2006 |
| WO | WO-2008035631 A1 | 3/2008 |
| WO | WO-2008105931 A2 | 9/2008 |
| WO | WO-2008141207 A1 | 11/2008 |
| WO | WO-2009060620 A1 | 5/2009 |
| WO | WO-2010050448 A1 | 5/2010 |
| WO | WO-2011133902 A2 | 10/2011 |
| WO | WO-2012017925 A1 | 2/2012 |
| WO | WO-2012019160 A1 | 2/2012 |

OTHER PUBLICATIONS 201207756-6, "Search Report dated Nov. 29, 2013", Nov. 29, 2013,5.
Anton Is, Kathryn et al., "Analysis of derivated peptides by capillary electrophoresis", Journal of Chromatoaraohv A vol. 661, 1994, 279-285.
AU2011242496, "Notice of Opposition dated", Feb. 18, 2016, 1 Page.
AU2011242496, Notice of Withdrawal of Opposition dated Mar. 14, 2017, 3 pages.
Barnett, R. et al., "Antibody Production in Chinese Hamster Ovary Cells Using an Imparied Selectable Marker", Chapters, Anibody Expression and Engineering, Wang, H. et al., ACS Symposium Series, ACS, 1995, 27-40.
Barrett, Shawn, "Integrated Medium and Feed Design for Five-Fold IGG Titer Improvement", Cell Culture Enaineering X11 Abstract : Poster No. 91, 2010, 140.
Bibila, T. et al., "In Pursuit of the Optimal Fed-Batch Process for Monoclonal Antibody Production", Biotechnol. Proa. vol. 11 (1), 1995, 1-13.
Cell Discory Research Products Catalog 2009-2010, Lanza Walkersville Inc., 2009, 9 Pages.

(Continued)

*Primary Examiner* — Sudhakar Katakam

(57) ABSTRACT

Cell culture media, concentrated media and feeds, methods of manufacturing cell culture media and feeds, and methods of culturing cells are provided. One or more small peptides, including dipeptides are added to the cell culture media to provide improved stability and improved conditions for culturing cells.

12 Claims, 7 Drawing Sheets

(56) References Cited

OTHER PUBLICATIONS

Christie, A. et al., "Glutamine-based dipeptides are utilized in mammalian cell culture by extracellular hydrolysis catalyzed by a specific peptidase", Journal of Biotechnology, vol. 37, 1994, 277-290.

Daabees, T. et al., "L-Aianyi-1-Tyrosine as a Tyrosine Source During Intravenous Nutrition of the Rat", The Journal of Nutrition Jul. 1978, 1104-1113.

Daabees, Tahia et al., "L-Aianyi-L-Tyrosine as a Tyrosine Source During Total Parenteral Nutrition. Infusion at 0.5 and 2 mmoles/kg/day in Adult Rats", Pediat. Res., vol. 13, 1979, 894-899.

Daniel, H. et al., "From Bacteria to Man: Archaic Proton-Dependent Peptide Transporters at Work", Physiology, vol. 21, Apr. 2006, 93-102.

Declaration of AnQelo Perani, Aug. 16, 2016.

Dipeptiven concentrate for solution for infusion, Fresenius Kabi Austria GmbH, Oct. 2007, 2 Pages.

Dringen, R. et al., "Use of Dipeptides for the Synthesis of Glutathione by Astorglia-Rich Primary Cultures", J. Neurochemistry. vol. 69, No. 2, Aug. 1997, 868-874, XP055063791, ISSN: 0022-3042.

Druml, et al., "Utilization of tyrosine dipeptides and acetyltyrosine in normal and uremic humans", American Journal of PhysioloaY. vol. 260 (2 Pt.1 ), 1991, E280-E285.

Druml et al., Utilization of tyrosine-containing dipeptides and N-acetyl-tyrosine in hepatic failure, Hepatology, vol. 21, No. 4, 1995, pp. 923-928.

Earle F R., et al., "Compositional Data on Sunflower Seed," JAOCS, vol. 45, Dec. 12, 1968, pp. 876-879 (Year: 1968).

EP11772796.6, "Extended EP Search Report dated Jun. 3, 2013", Jun. 3, 2013, 6 Pages.

EP16192190.3, "Extended European Search Report dated", Apr. 11, 2017, 11 Pages.

EP16198499.2, "Extended European Search Report dated", Mar. 3, 2017, 6 Pages.

Fernandez, P.A. et al., "Effect of Amino Acids and Peptides on Growth of Pediococcus Pentosaceus From Wine", Latin American Applied Research vol. 33, 2003, 225-229.

Fitzgerald et al., "Reparative Properties of a Commercial Fish Protein Hydrolysate Preparation", Gut, vol. 54, 2005, pp. 775-781.

Franek, F. et al., "Specific Effects of Synthetic Oligopeptides on Cultured Animal Cells", Biotechnoloaical Proaress vol. 18, No. 1, Jan. 3, 2002, 155-158.

Fratelli, et al., Biotechnol. Prog., vol. 21, 2005, 756-761.

Furst, et al., "Amino-Acid Substrates in New Bottles: Implications for Clinical Nutrition in the 21st Century", Nutrition, vol. 16, Nos. 7/8, 2000, 603-606.

Furst et al., Dipeptide in clinical nutrition, Proc. Nutr. Soc., 1990, 49, 343-359.

Furst, et al., "Synthetic Dipeptides—A New Dimension in Clinical Nutrition", The Parenteral and Enteral Nutrition Society of Asia vol. 1, No. 3, Sep.-Dec. 2000, 2 pages.

Furst, P. "Old and New Substrates in Clinical Nutrition", The Journal of Nutrition. vol. 128, 1998, 789-796.

Furst, Peter, "New Developments in Glutamine Delivery", Glutamine Metabolism: Nutritional and Clinical Significance 2001, 2562S-2568S.

Gibco., "A Guide to Serum-Free Cell Culture", Gibco Cell Culture/Invitrogen, 2003, 11 Pages.

Gibco, "GiutaMax® I (1 OOX)", Cat. No. 36050-061, Jun. 2003, 1.

Gibco, "What happens when you pair the finest base medium with the perfect feed supplement?", Gibco® CD OptiCHO™ Medium and CHO CD EfficientFeed™ Kit, Invitrogen; Cell Culture, 2008, 1-4.

Gibco(R) Advanced RPMI 1640 and DMEM/F-12 Product News, Invitrogen Corporation, 2004, 4 Paqes.

Gibco(R) CD CHO Medium, Invitroaen Corporation, Dec. 2009, 2 Pages.

Gong X., et al., "Fed-batch culture optimization of a growth-associated hybridoma cell line in chemically defined protein-free media," Cytotechnology, (2006), 52:25-38.

Greene, J. et al., "Rapid and Precise Determination of Cellular Amino Acid Flux Rates Using HPLC with Automated Derivatization with Absorbance Detection", Agilent Technologies, Application Note, Pharmaceutical Food Industries, Feb. 6, 2009, 1-8.

Hanigan, M. et al., "Extracellular Glutathione is a Source of Cysteine for Cells That Express gamma-Giutamyl Transpeptidase", Biochemistry, vol. 32, 1993, 6302-6306.

Hata, et al., "Chemically defined medium for the production of biologically active substances of CHO cells", Cvtotechnoloav. vol. 10, 1992, 9-14.

https://en.wiki ped ia.org/wiki/Parenteral_nutrition#Prepared_solutions, 2017, ten pages.

Immamoto, et al., "Advantage of Alagln as an Additive to Cell Culture Medium: Application to Anti-CD20 Chimeric Antibody-Production Potelligent TM CHO Cell Lines", In: Kamihara M, Katakura Y., Ito A. (eds) Animal Cell Technolog~: Basic & Applied Aspects. Animal Cell Technology: Basic & Applied Aspects vol. 16 Springer Dordrecht, Jan. 1, 2010, 65-71, XP001526136, ISBN: 978-90-481-3892-0.

Iscove, N.N. and Melchers, F., "Complete replacement of serum by albumin, transferrin and soybean lipid in cultures of lipopolysaccharide-reactive B lymphocytes", J. Exp. Medicine, vol. 147, pp. 923-933, 1978.

Iscove, N.N., Guilbert, L.J., and Weyman, C., "Complete replacement of serum in primary cultures of erythropoietin dependent red cell precursers [CFU-E] by albumin, transferrin, iron, unsaturated fatty acid, lecithin and cholesterol", Exp. Cell Research, vol. 126, pp. 121-126, 1980.

Ito, T. et al., "The Growth-Stimulating Activity of Peptides on Human Hematopoietic Cell Cultures", Experimental Cell Research vol. 56, 1969, 10-14.

Kelley B: "Industrialization of mAb production technology the bioprocessing industry at a crossroads," mAbs, 2009, vol. 1, No. 5, pp. 443-452.

Kihara H., et al., "Peptides and Bacterial Growth", The Journal of Biological Chemistry, May 1960, vol. 235, No. 5, pp. 1409-1414.

Krasinska, K. et al., "Quantitative LC-MS/MS Analysis of proteins and peptides", Standford University Workshop. http://mass-spec.stanford.edu/UsersMtQ 090903.html., Sep. 3, 2009, 1-31.

Minamoto, Y. et al., "Development of a serun-free and heat-sterilizable medium and continuous high-density cell culture", CytotechnoloaY. vol. 5, 1991, S35-51.

Mohabbat, T. et al., "Simultaneous determination of 33 amino acids and dipeptides in spent cell culture media by gas chromatography-flame ionization detection following liquid and solid phase extraction", Journal of Chromatoaraphy B vol. 862, 2008, 86-92.

Morrow, K. John J., "Advances in antibody manufacturing using mammalian cells", Biotechnology Annual Review, 2007, vol. 13, 95-113.

O'Neil, M.J. (Ed.), The Merck Index: An Encyclopedia of Chemicals, Drugs, and Biologicals (14th ed.) NJ: Merck 2006, 467-468, 1690-1691.

P. Stehle, Infusiontherapie, 15:27-32 (Jan. 1988), English translation.

P. Stehle, Infusiontherapie, 15:27-32 (Jan. 1988), German language copy.

PCT/US2011/033630, "International Preliminary Report on Patentability dated Oct. 23, 2012", 1-7.

PCT/US2011/033630, "International Search Report and Written Opinion dated Aug. 2, 2012", Feb. 8, 2012, 1-13.

Pollack, et al., "Cystinhaltige kurzkettige Peptide also potentielle Cystinquelle in der parenteralen Ernahrung", Z. Emahrungswiss vol. 28, 1989, 191-200.

Product Information L-Tyrosine T3 754, Siama-Aidrich, 2006, 1 Page.

Qu, Jun, et al. "Validated Quantitation of Underivatized Amino Acids in Human Blood Samples by Volatile ion-Pair Reversed-Phase Liquid Chromatography Coupled to Isotope Dilution Tandem Mass Spectrometry", Anal. Chem. vol. 74 2002, 2034-2040.

Roth, E. et al., "Influence of Two Glutamine-Containing Dipeptides on Growth of Mammalian Cells", In Vitro Cellular & Develoomental BioloaY. vol. 24, No. 7, Jul. 1998, 696-698.

(56) References Cited

OTHER PUBLICATIONS

SAFC Biosciences®, , "Giutamine-S Stability", Technical Bulletin, 2006, 1-4.
SAFC Biosciences®, Product Information, "EX-CELL™ CD Hydrolysate Fusion Chemically Defined, Animal-Component Free", www.safcbiosciences.com, Catalog No. 14700C, 2009.
Sigma Iscove's Modified Dulbecco's Medium, 2006, 2 pages.
Sigma-Aldrich: "Cysteine in Cell Culture," 2 pages, online Dec. 4, 2008 (Year: 2008).
Statutory Declaration of Dr. Stephen F. Gorfien dated Feb. 28, 2017.
Statutory Declaration of Fiona Grigg, Feb. 28, 2017.
Statutory Declaration of George Mokdsi, Feb. 28, 2017.
Stehle et al, "In Vivo Utilization of Cystine-Containing Synthetic Short-Chain Peptides after Intravenous Bolus Injection in the Rat" American Institute of Nutrition, 1470-1474, 1988 (Year: 1988).
Stehle, Peter, "Preparation of Short-Chain Peptides—A Prerequisit for the Use Thereof in Artificial Nutrition", Infusionstherapie, vol. 15, Jan. 1988, 27-32.
Tabata, et al., "Fermentative Production of L-Ianyi-L-Giutamine by a Metabolically Engineered *Escherichia coli* Strain Expressing L-Amina Acid alpha-Ligase", Agglied and Environmental MicrobioloaY. vol. 73, No. 20, Oct. 2007, 6378-6385.

Tatsuya, 1., "Chemical Synthesis of Proteins in Solution Using Chloroform-Trifluoroethanol and Chloroform-Phenol Mixed Solvents: Synthesis of Human Amyloid 13-Peptides, Midkine, Pleiotrophin and Leptin", Osaka University Knowledge Archive, http://hdl.handle.next/11 094/44589, Jul. 3, 2003, 5 pages.
Technical Manual Supplements for cell culture, fermentation, and diagnostic media, Sheffield Bioscience, Mar. 2011, 43 pages.
Tiscornia, G. et al., "Production and purification of lentiviral vectors", Nature Protocols, vol. 1, No. 1, Jun. 27, 2006, 241-245.
Van Wandelen, Charlie et al., "Using quaternary high-performance liquid chromatography eluent systems for separating 6-aminoquinolyi-N-hydroxysuccinimidyl cabramate-derivatized amino acid mixtures", Journal of Chromatoaraohv A vol. 763, 1997, 11-22.
Vazquez, et al., "Dipeptides in Parenteral Nutrition: from Basic Science to Clinical Applications", Nutrition in Clinical Practice vol. 8, No. 3, Jun. 1993, 95-105.
Whitford, W., "Supplementation of Animal Cell Culture Media", BioProcess International. Supplement, Jun. 2005, 28-36.
Young, C. et al., "Human Embryonic Stem Cell Lines Generated without Embryo Destruction", Cell Stem Cell, vol. 2(2), Feb. 7, 2008, pp. 113-117.
Bansal et al., Variables Affecting Reconstitution Time of Dry Powder for Injection, Pharm. Tech., Jul. 2008, vol. 32, Issue 7, 3 pages. Retrieved from internet Aug. 19, 2017.

\* cited by examiner

CELL CULTURE MEDIUM COMPRISING SMALL PEPTIDES

CROSS-REFERENCE TO RELATED APPLICATIONS

This application is a continuation of U.S. patent application Ser. No. 15/349,791, filed Nov. 11, 2016, which is a divisional of U.S. patent application Ser. No. 13/092,016, filed Apr. 21, 2011, which claims priority to U.S. Provisional Application No. 61/327,644, filed Apr. 23, 2010, all of which disclosures are herein incorporated by reference in its entirety.

BACKGROUND

Cell culture media provide the nutrients necessary to maintain and grow cells in a controlled, artificial and in vitro environment. Nutrient formulations, pH, and osmolality of cell culture media vary in accordance with parameters such as cell type, cell density, and the culture system employed.

Media formulations have been used to cultivate a number of cell types including animal, plant and bacterial cells. Cultivated cells have many uses including the study of physiological processes and the production of useful biological substances. Examples of such useful products include polypeptides, such as monoclonal antibodies, hormones, growth factors, enzymes, and other polypeptides of interest. Such products have many commercial and therapeutic applications and, with the advent of recombinant DNA technology, cells can be engineered to produce large quantities of these products. Cultured cells are also routinely used for the isolation, identification and growth of viruses which can be used as vectors and/or vaccines. Thus, the ability to cultivate cells in vitro is not only important for the study of cell physiology, but is also necessary for the production of useful substances which may not otherwise be obtained by cost-effective means.

Cell culture media formulations have been well documented in the literature and a number of media are commercially available. In early cell culture work, media formulations were based upon the chemical composition and physicochemical properties (e.g., osmolality, pH, etc.) of blood and were referred to as "physiological solutions" Ringer, S., J. Physiol. 3:380-393 (1980); Waymouth, C., In: Cells and Tissues in Culture, Vol. 1, Academic Press, London, pp. 99-142 (1965); Waymouth, C., In Vitro 6:109-127 (1970). However, cells in different tissues of the mammalian body are exposed to different microenvironments with respect to oxygen/carbon dioxide partial pressure and concentrations of nutrients, vitamins, and trace elements, accordingly, successful in vitro culture of different cell types will often require the use of different media formulations. Typical components of cell culture media include amino acids, organic and inorganic salts, vitamins, minerals, trace metals, sugars, lipids, and nucleic acids, the types and amounts of which may vary depending upon the particular requirements of a given cell or tissue type.

Glutamine is routinely used in cell culture media because it has been shown to be a major energy source for cultured cells. In 1959, Eagle showed that the amount of glutamine necessary for optimal growth of mammalian cell cultures is 3 to 10 times greater than the amount of other amino acids. Eagle et al., Science 130:432-37 (1959). However, glutamine is unstable in aqueous solution and at elevated temperatures, forming pyroglutamate and ammonia, which can be toxic to certain cells. Roth et al., In Vitro Cellular & Developmental Biology 24(7):696-98 (1988). Therefore, glutamine is typically added to cell culture medium immediately before use.

Alternatively, to avoid the formation of toxic substances like pyroglutamate and ammonia, glutamine-containing dipeptides, such as alanyl-glutamine or glycyl-glutamine, can be used in cell culture media instead of glutamine Roth et al., In Vitro Cellular & Developmental Biology 24(7): 696-98 (1988). Glutamate has also been used instead of glutamine to reduce the accumulation of ammonia in the cell culture medium See Cell Culture Technology for Pharmaceutical and Cell-Based Therapies, 52, Sadettin Ozturk and Wei-Shou Hu eds., Taylor and Francis Group (2006).

Others have proposed acylating a dipeptide, such as alanyl glutamine, to make the dipeptide more stable under heat sterilization conditions. For example, U.S. Pat. No. 5,534,538 describes N-acyl dipeptides for use in enteral or parenteral nutrition where the N-acyl dipeptides are more stable under heat sterilization conditions than corresponding non-acylated dipeptides and where the N-acyl group advantageously delays splitting of the dipeptide until it reaches the kidneys. U.S. Pat. No. 5,534,538 also found that N-acyl alanyl glutamine was a suitable glutamine source for cell culture media, similar to the corresponding non-acylated dipeptide (alanyl glutamine), which was a known component of cell culture medium (see Roth et al. above). U.S. Pat. No. 5,534,538 further described the N-acyl dipeptides as advantageous over free dipeptides, at least in part, because of the increased stability of N-acyl dipetides under heat sterilization conditions. Thus, U.S. Pat. No. 5,534,538 actually teaches away from using dipeptides where the N-terminal amino acid has a free amino group.

Applicants have found that certain amino acids, like tyrosine, have limited solubility at the desired concentration for maximal cell growth or protein production. Applicants have also found that other amino acids, like cysteine, are unstable and prone to precipitation over time in aqueous cell culture medium, particularly in concentrated cell culture medium. Specifically, because cysteine has a thiol group, it is susceptible to an oxidation reaction in which two cysteine residues are linked together by a disulfide bond to form cystine $(SCH_2CH(NH_2)CO_2H)_2$. Cystine has low solubility in water and readily precipitates out of solution. As a result, it has not been possible to produce a shelf-stable, liquid cell culture medium containing concentrations of tyrosine and cysteine required for maximal cell growth and/or protein production.

Applicants have also tried to address this problem by using less than the desired concentration of tyrosine or cysteine in the aqueous cell culture medium. In so doing, it is possible to achieve an acceptable aqueous shelf life. However, this is accomplished at the expense of optimal cell growth, protein production or viral production. In other words, cell culture medium with lower concentrations of tyrosine and cysteine supports reduced cell growth and/or protein production as compared to cell culture medium with the optimal concentrations of tyrosine and cysteine.

Thus, there exists a current need for a medium, concentrated medium or concentrated feed supplement containing amounts of tyrosine and cysteine sufficient to support maximal cell growth and/or protein or viral production while avoiding the problems caused by the limited solubility of tyrosine or the limited stability of cysteine, including the tendency of cysteine to precipitate out of solution over time. In addition, there exists a need for such a feed supplement to be in a concentrated form, so that its addition would not greatly add volume to the final cell culture system. There also exists a need that when such nutrient feeds are added, the pH and osmolality of the resulting system be automatically balanced, and that the medium or concentrated feed be available in a liquid or a dry format. Lastly, there exists a need for a single-regimen, concentrated feed supplement comprising amounts of cysteine and tyrosine sufficient to support maximal cell growth and/or protein production, and/or expressed protein of high quality.

SUMMARY

The compositions of the invention are directed, in part, to cell culture media, concentrated media, or concentrated feed supplements comprising concentrations of cysteine and tyrosine that support maximal cell growth and/or protein, or viral production while avoiding the problems caused by their limited solubility and stability. In one aspect, the media, concentrated feed supplements, or concentrated media may be serum-free compositions. In one aspect, the compositions may comprise human serum components, like human serum albumin. In a further aspect, the human serum albumin may be recombinant, (r-human serum albumin), derived from recombinant sources, in some preferred cases, form plant sources like rice, corn, wheat, potato, or from fungal sources, or from yeast or other equivalent microorganisms well-known to be used in the art (xeno-free culture). In another aspect, the media, concentrated feed supplements, or concentrated media may be protein-free compositions. In yet another aspect, the media, concentrated feed supplements, or concentrated media may be protein-hydrolysate free compositions, and further, may be free of fractions of protein-hydrolysates. In a certain aspect, the media, concentrated feed supplements, or concentrated media may be serum-free, protein-free, and protein hydrolysate-free compositions. In a preferred aspect, these compositions may comprise components that are chemically-defined, serum-free, protein-free and free of any protein hydrolysates, or fractions thereof. In certain embodiments, the cell culture medium, concentrated medium or cell culture feed supplement having one or more small peptides, or one or more dipeptides, further does not contain one or more of the following: lipids, hydrolysates or a fraction thereof, or growth factors.

The invention is also directed, in part, to methods for analyzing the compositions described above for the presence or absence of a short peptide comprising cysteine or tyrosine. The analysis of the media is performed by any known method in the art, for instance, by mass spectrometry (LCMS), capillary electrophoresis or HPLC.

In particular, the present disclosure is directed to a cell culture medium, a concentrated feed, or a cell culture supplement comprising one or more small peptides having two to six amino acids, as defined later in the application. Therefore, the present disclosure provides a cell culture medium, a concentrated feed, or a cell culture supplement, wherein the medium, feed or supplement comprises one or more small peptides selected from $X_{1-5}$-tyrosine, $X_{1-5}$-cysteine, tyrosine-$X_{1-5}$, and cysteine-$X_{1-5}$, or any small peptide where cysteine or tyrosine is anywhere within the short peptide of 1 to 6 amino acids (for e.g., X-cysteine-$X_{1-4}$, X-tyrosine-$X_{1-4}$, etc.) or a salt thereof, wherein X is any amino acid, and wherein the N-terminal amino acid of the short peptide has a free amino group. In one embodiment, X is alanine or glycine. In another embodiment X is serine, valine, proline, aspartic acid, or glutamic acid. In a particular embodiment, the present disclosure provides a cell culture medium, a concentrated feed, or a cell culture supplement, wherein the medium, feed or supplement comprises one or more dipeptides selected from X-tyrosine, X-cysteine, tyrosine-X, and cysteine-X, or a salt thereof, wherein X is any amino acid, and wherein the N-terminal amino acid of the dipeptide has a free amino group. In one embodiment, X is alanine or glycine. In another embodiment X is serine, valine, proline, aspartic acid, or glutamic acid. In yet another embodiment, the one or more dipeptides are alanyl tyrosine and/or alanyl cysteine. The cell culture medium, concentrated feed, or cell culture supplement may be a liquid solution or a dry powder, such as a dry powder media (DPM) or an agglomerated powder (AGT™). In one embodiment, the liquid solution is stored at 2-8° C. and remains free of precipitate for over 12 months.

In one embodiment of the invention, the concentration of tyrosine (as comprised within the small peptide), in solution, in a medium, feed or supplement, will be greater than the concentration of tyrosine that would remain soluble in an identical solution, if the tyrosine were present as a monomer (that is, tyrosine in a small peptide may make the solution "supersaturated for tyrosine"). In one embodiment, the solution will have between about 1 and at least about 100 times, or about 1 and at least about 25 times, the soluble tyrosine concentration as would be capable with the monomer. For example, the concentration of small peptides or dipeptides in some cell culture media, concentrated feeds or supplements may be about 1 to at least about 5 times, about 1 to at least about 10 times, about 1 to at least about 15 times, about 1 to at least about 20 times, about 1 to at least about 30 times, about 1 to at least about 40 times, about 1 to at least about 50 times, about 1 to at least about 60 times, about 1 to at least about 70 times, about 1 to at least about 80 times, about 1 to at least about 90 times, about 1 to at least about 100 times, about 10 to at least about 20 times, about 10 to at least about 30 times, about 10 to at least about 40 times, about 10 to at least about 50 times, about 10 to at least about 60 times, about 10 to at least about 70 times, and so on, the soluble tyrosine concentration as would be capable with the monomer.

In one embodiment of the invention, the concentration of cysteine (as comprised within the small peptide), in solution, in a medium, feed or supplement, will be greater in the solution than the concentration of cysteine that would remain soluble in an identical solution if the cysteine were present as a monomer (that is, cysteine in a small peptide may make the solution "supersaturated for cysteine"). In one embodiment, the solubility of cysteine (or lack thereof) would include, for example, loss of solubility caused by conversion of cysteine to cystine. In one embodiment, the solution will comprise at least, between about 1 and about 25 times, the soluble cysteine concentration capable with the monomer. For example, the concentration of small peptides or dipeptides in some cell culture media, concentrated feeds or supplements may be at about 1 to at least about 5 times, about 1 to at least about 10 times, about 1 to at least about 15 times, about 1 to at least about 20 times, about 1 to at least about 30 times, about 1 to at least about 40 times, about 1 to at least about 50 times, about 1 to at least about 60 times, about 1 to at least about 70 times, about 1 to at least about 80 times, about 1 to at least about 90 times, about 1 to at least about 100 times, about 1 to at least about 110 times, about 10 to at least about 20 times, about 10 to at least about 30 times, about 10 to at least about 40 times, about 10 to at least about 50 times, about 10 to at least about 60 times, about 10 to at least about 70 times, about 10 to at least about 80 times, about 10 to at least about 90 times, about 10 to at least about 100 times, about 10 to at least about 110 times, and so on, the soluble cysteine concentration as would be capable with the monomer. In one embodiment, the solution is supersaturated for both tyrosine and cysteine.

In one embodiment, the solution will be supersaturated for both tyrosine and cysteine in, for example, the ranges described above for each of tyrosine or cysteine alone.

In one embodiment, the addition of the concentrated feeds, media or supplements described above could reduce the volume of supplementation to a culture system, for e.g., a fed-batch culture, which may already be in progress. The culture may be in progress for a few hours to a few days. In another embodiment, increasing the solubility of the cysteine and tyrosine comprised within small peptides allows for the design of single part concentrated feeds, which may also be pH neutral, which is part of the invention. The invention is directed in part to preparation of single regimen concentrated feeds, concentrated media and concentrated supplements comprising cysteine and tyrosine comprised within a small peptide, to increase their solubility and stability within the composition.

The cell culture medium, concentrated feed or cell culture supplement having one or more small peptides, or one or more dipeptides optionally comprises one or more of the following: a carbohydrate, a vitamin, a salt, an inorganic element, a buffering agent, and an amino acid, or a salt thereof. In one embodiment the carbohydrate is a hexose sugar. Alternately, pentose, hexose, or their derivatives or other equivalents may be used. In some instances, oligosaccharides or their derivatives may be used; or, the hexose may be selected from the group consisting of glucose, galactose, fructose and maltose. In a particular embodiment, the carbohydrate is glucose.

In one embodiment, the amino acid, or salt thereof, is one or more of arginine, asparagine, aspartic acid, cysteine, glutamic acid, glutamine, histidine, isoleucine, leucine, lysine, methionine, phenylalanine, proline, serine, threonine, tryptophan, tyrosine, and valine.

In one embodiment, the cell culture medium, concentrated feed or cell culture supplement comprises a 1) first dipeptide, X-tyrosine, or a salt thereof, and a second dipeptide, X-cysteine, or a salt thereof, wherein X is alanine or glycine and wherein the alanine or glycine has a free amino group, 2) a carbohydrate, such as glucose, and 3) an amino acid, or a salt thereof. The amino acid, or a salt thereof, may comprise one or more of arginine, asparagine, aspartic acid, cysteine, glutamic acid, histidine, isoleucine, leucine, lysine, methionine, phenylalanine, proline, serine, threonine, tryptophan, tyrosine, and valine.

In one embodiment, the cell culture medium, concentrated feed or cell culture supplement has one or more small peptides, or one or more dipeptides, suitable for culturing a bacterial cell, a yeast cell, a plant cell, or an animal cell, such as an insect cell (e.g., *Drosophila* cells, *Spodoptera* cells or *Trichoplusia* cells), a nematode cell (e.g., *C. elegans* cells) or a mammalian cell (e.g., CHO cells, COS cells, VERO cells, BHK cells, AE-1 cells, SP2/0 cells, L5.1 cells, PerC6, hybridoma cells, HEK 293, including human cells).

In certain embodiments, the cell culture medium having one or more small peptides or one or more dipeptides is a 1× formulation. In other embodiment, the cell culture medium is concentrated as a 2× or greater formulation, as discussed elsewhere in this application. In certain embodiments, the one or more small peptides or dipeptides, such as X-tyrosine, X-cysteine, tyrosine-X, or cysteine-X, are present in the cell culture medium at a concentration of about 1 g/L to about 16 g/L, about 1 g/L to about 10 g/L, about 1 g/L to about 5 g/L, about 2.5 g/L to about 16 g/L, about 2.5 g/L to about 10 g/L, about 2.5 g/L to about 5 g/L, or about 2.5 g/L to about 8.5 g/L.

In another aspect, the disclosure provides a method of culturing a cell, comprising contacting the cell with the small peptide- or dipeptide-containing cell culture medium described herein under conditions supporting the cultivation of the cell. Any cell may be cultured according to the present methods, particularly bacterial cells, yeast cells, plant cells or animal cells. In one embodiment, the animal cell for culturing according to the present methods is an insect cell (e.g., *Drosophila* cells, *Spodoptera* cells or *Trichoplusia* cells), a nematode cell (e.g., *C. elegans* cells) or a mammalian cell (e.g., CHO cells, COS cells, VERO cells, BHK cells, AE-1 cells, SP2/0 cells, L5.1 cells, PerC6, hybridoma cells, HEK 293 or other human cells).

In another embodiment, the method of culturing a cell comprises contacting the cell with a basal cell culture medium under conditions supporting the cultivation of the cell and supplementing the basal cell culture medium with a cell culture medium, a cell culture supplement, or a cell culture feed, having one or more small peptides or one or more dipeptides, as described herein. In one embodiment, the one or more dipeptides selected from X-tyrosine, X-cysteine, tyrosine-X, or cysteine-X, or a salt thereof, wherein X is selected from alanine, glycine, serine, valine, proline, aspartic acid, or glutamic acid and wherein the N-terminal amino acid of the one or dipeptides has a free amino group. In another embodiment, the one or more dipeptides are alanyl tyrosine and/or alanyl cysteine.

In one embodiment, the basal cell culture medium is supplemented with a solution, comprising cysteine and tyrosine in a small peptide, on more than one day, wherein the solution may be a concentrated medium, or a concentrated feed supplement. In certain embodiments, applicants may refer to the use of media, feed, supplements, or other solutions which comprise small peptides (including, for example, solutions comprising dipeptides which comprise at least one tyrosine or cysteine residue). Indeed, one embodiment of applicants' invention is the use of such solutions in the culturing of cells. In that respect, one of skill in the art will appreciate that in certain recitations herein, Applicants may refer to a specific supplement, media(um), feed or solution merely as an example of an embodiment that could equally apply to any of the types of solutions described herein. For example, one of skill in the art would understand that a recitation of a "supplement" with a specific amino acid composition can equally describe a "feed" with a like composition and vice versa.

The basal cell culture medium, concentrated medium, concentrated feed or supplement may comprise a small peptide- or dipeptide-containing medium or feed on day 0, day 1, day 2, day 3, day 4 or 5 days after starting the cell culture and is supplemented daily thereafter through day 13 or 14 or until the viability of the culture drops below a pre-determined level (eg. 50%). The basal cell culture medium is optionally supplemented with the small peptide- or dipeptide-containing cell culture medium at about 2% of the total volume of the basal cell culture medium. In one embodiment, the cell produces a protein, a peptide, a small RNA (for e.g., miRNA, siRNA, etc). By protein is meant, a recombinant protein or a naturally occurring protein. By protein, whether recombinant or natural, is also meant a full-length protein or a part thereof (like a domain, a motif, a polypeptide chain or polypeptide fragment). By protein, whether recombinant or natural, is also meant an intracellular protein, an extracellular protein, a secreted protein, hormone, cytokine, receptor, extracellular matrix protein, an immunoglobulin or a part of the immunoglobulin, or a fragment thereof. Preferably, the protein yield may be higher with the cell culture medium, feed or supplement comprising the short peptides, or dipeptides of the invention. In a specific aspect, for instance, the protein yield for an immunoglobulin may be greater than 3000 mg/L of immunoglobulin, after at least 14 days in culture. In another embodiment, the cell can produce a virus or a VLP (virus like particle). In yet another embodiment, the cell may produce a desired cell product like a vitamin, a metabolite, a glycoprotein, a carbohydrate, a lipid, or a lipoprotein. In another embodiment, the cell itself is grown to be harvested. The media and feed supplement compositions of the invention comprise concentrations of cysteine and tyrosine that support maximal cell growth for viral or VLP production, or maximal vitamin production, or glycoprotein, or vaccine production, etc., while avoiding the problems caused by their limited solubility.

Any cell may be cultured according to the present methods, for instance bacterial cells, yeast cells, plant cells, insect cells or animal cells, including mammalian cells. In one embodiment, the animal cell for culturing according to the present methods is an insect cell (e.g., *Drosophila* cells, *Spodoptera* cells or *Trichoplusia* cells), a nematode cell (e.g., *C. elegans* cells) or a mammalian cell (e.g., CHO cells, COS cells, VERO cells, BHK cells, AE-1 cells, SP2/0 cells, L5.1 cells, PerC6, hybridoma cells, or other human cells). In one embodiment, the cell is a CHO cell.

Another aspect provides a method of preparing a cell culture medium, comprising combining one or more small peptides or dipeptides, as described herein, with a carbohydrate, such as glucose, and at least one amino acid or salt thereof, such as arginine, asparagine, aspartic acid, cysteine, glutamic acid, histidine, isoleucine, lysine, methionine, phenylalanine, proline, hydroxyproline, serine, threonine, tryptophan, tyrosine, glutamine, and valine. In one embodiment, the one or more dipeptides are selected from X-tyrosine, X-cysteine, tyrosine-X, or cysteine-X, or a salt thereof, wherein X is selected from alanine, glycine, serine, valine, proline, aspartic acid, or glutamic acid and wherein the N-terminal amino acid of the one or dipeptides has a free amino group. In another embodiment, the one or more dipeptides are alanyl tyrosine and/or alanyl cysteine.

In other embodiments, the cell culture medium prepared according to this method is concentrated as a 2× or greater formulation, as discussed elsewhere in this application. In certain embodiments, the one or more small peptides or dipeptides, such as alanyl tyrosine and/or alanyl cysteine, are present in the cell culture medium prepared according to this method.

For example, the concentration of small peptides or dipeptides in some cell culture media or the concentrated media or feeds may be about 0.5 g/L to about 30 g/L, about 0.5 g/L to about 25 g/L, about 0.5 g/L to about 20 g/L, about 0.5 g/L to about 16 g/L, about 0.5 g/L to about 10 g/L, about 0.5 g/L to about 5 g/L, about 0.5 g/L to about 4 g/L, about 1 g/L to about 30 g/L, about 1 g/L to about 20 g/L, about 1 g/L to about 16 g/L, about 1 g/L to about 10 g/L, about 1 g/L to about 5 g/L, about 2.5 g/L to about 30 g/L, about 2.5 g/L to about 20 g/L, about 2.5 g/L to about 16 g/L, about 2.5 g/L to about 10 g/L, about 2.5 g/L to about 5 g/L, or about 2.5 g/L to about 4.5 g/L, about 5 g/L to about 30 g/L, about 5 g/L to about 25 g/L, about 5 g/L to about 20 g/L, about 5 g/L to about 16 g/L, about 5 g/L to about 10 g/L, about 5 g/L to about 5 g/L, about 5 g/L to about 4 g/L, and so on.

Another aspect provides a composition comprising the small peptide- or dipeptide-containing cell culture medium described herein and at least one cell, as described above. In one embodiment, the at least one cell is a CHO cell.

Yet another aspect is directed to kits for use in the cultivation of a cell. The kit may comprise one or more containers containing the small peptide- or dipeptide-containing cell culture medium described herein. The kit optionally comprises at least one additional component selected from at least one growth factor, at least one animal tissue extract, at least one animal organ extract, at least one animal gland extract, at least one enzyme, at least one protein, at least one vitamin, at least one cytokine, at least one lipid, at least one trace element, at least one extracellular matrix component, at least one buffer, at least one antibiotic, and at least one viral inhibitor. The kit may also comprise one or more cells or cell types.

Another aspect is directed to methods of producing a virus or a VLP using the small peptide- or dipeptide-containing cell culture media described herein. Specifically, the method comprises (a) contacting a cell (e.g., a mammalian cell) with a virus under conditions suitable to promote the infection of the cell by the virus; and (b) cultivating the cell in the culture media described herein under conditions suitable to promote the production of virus by the cell. In one embodiment, the cell that produces the virus or VLP is a mammalian cell, such as a CHO cell, or an insect cell, or a plant cell, or a fungal cell. In another embodiment, a non-mammalian virus or VLP is engineered such that it can infect a mammalian host cell, for e.g., a human cell.

In yet another aspect, the disclosure provides methods of producing a polypeptide, such as an immunoglobulin or a fragment thereof, using the small peptide- or dipeptide-containing cell culture media described herein. Specifically, the method comprises cultivating a cell that has been genetically engineered to produce a polypeptide in the dipeptide-containing culture media under conditions suitable for expression of the polypeptide by the cell. In one embodiment, the cell is a mammalian cell, such as a CHO cell.

Therefore, one aspect of the invention is directed to a cell culture medium, concentrated feed, or concentrated feed supplement comprising at least one small peptide, said peptide comprising at least two amino acids, wherein at least one of the amino acids is a cysteine or a tyrosine. Another aspect of the invention is directed to a cell culture medium, concentrated feed, or concentrated feed supplement described above, wherein at least one of the remaining amino acids of the small peptide are selected from the group consisting of alanine, glycine, serine, valine, proline, aspartic acid, and glutamic acid. Yet another aspect of the invention, at least one of the remaining amino acids of the small peptide is alanine or glycine. Another aspect of the invention is directed to a cell culture medium, concentrated feed, or concentrated feed supplement medium described above, wherein at least one of the small peptides is a dipeptide selected from the group consisting of X-tyrosine, X-cysteine, tyrosine-X, and cysteine-X, or a salt thereof, and wherein X is selected from the group consisting of alanine, glycine, serine, valine, proline, aspartic acid, and glutamic acid, and/or, and wherein the N-terminal amino acid of the one or small peptides has a free amino group. In one aspect the X is alanine or glycine.

In some aspects of this invention, the small peptide may be either a dipeptide, a tripeptide, a tetrapeptide, a pentapeptide, a hexapeptide, a heptapeptide, an octapeptide, a nonapeptide, or a decapeptide; or, the small peptide may be at least about two to ten amino acids in length; or in some aspects, the small peptide is at least about ten amino acids in length. In some aspects, the short peptide may comprise two, three, four, five or six amino acids.

In other aspects, the cell culture medium is a liquid solution.

In any one of the cell culture medium described above, the cell culture medium, concentrated feed, or concentrated feed supplement is a dry powder or a granulated dry powder.

In a further aspect, any one of the cell culture medium described above may comprise a carbohydrate and an amino acid, or a salt thereof. In one embodiment, the carbohydrate is a hexose. In other embodiments, the amino acid, or salt thereof, is any one or more of arginine, asparagine, aspartic acid, cysteine, glutamic acid, histidine, isoleucine, lysine, methionine, phenylalanine, proline, hydroxyproline, serine, threonine, tryptophan, tyrosine, and valine. In a further embodiment, the media further comprises a vitamin, a salt, a buffering agent, or an inorganic element.

In some aspects described above, the cell culture medium, concentrated feed, or concentrated feed supplement does not contain a lipid, a hydrolysate or a fraction thereof, or a growth factor. In other aspects described above, the cell culture medium, concentrated feed, or concentrated feed supplement does not contain a protein. Thus in some preferred aspects, the cell culture medium, concentrated feed, or reconstituted medium comprising a small peptide may be serum-free, protein-free and/or hydrolysate-free.

In particular aspects, the cell culture medium, concentrated feed, or concentrated feed supplement is concentrated as a 2× or greater formulation. In a preferred aspect, the cell culture medium, concentrated feed, or concentrated feed supplement described above comprises one or more dipeptides, which may be either alanyl tyrosine and/or alanyl cysteine and/or alanyl cystine dimer. In a preferred aspect, the one or more dipeptides may be present at a concentration of about 1 g/L to about 16 g/L; or the one or more dipeptides may be present at a concentration of about 2.5 g/L to about 8.5 g/L. In one aspect, the liquid solution stored at 2-8° C. remains free of precipitate for over 12 months.

The present invention is also directed to a method of culturing a cell, comprising contacting the cell with a basal cell culture medium under conditions supporting the cultivation of the cell and supplementing the basal cell culture medium with a concentrated feed or medium described above. The supplementation may be done during a fed-batch culture; or performed in addition to an existing feeding schedule; or, the supplementation may be performed continuously as opposed to incrementally with bolus additions. In some cases, the basal cell culture medium may be supplemented with the concentrated feed or medium on more than one day; or, the supplementation of the basal cell culture medium may be done with a single concentrated feed, or with multiple concentrated feeds; or, the supplementation may occur either from day 0, day 1, day 2, day 3, day 4 or day 5 after starting the cell culture, and is supplemented daily thereafter through day 13 or 14; or, each supplementation may be about 1-10%, or about 5-20%, of the total starting volume of the basal cell culture medium.

In all aspects of the methods used herein, the cell may be an engineered cell; or the cell may be a recombinant cell; or the cell may be a plant cell, or the cell may be any one of an animal, a plant, an insect, an avian, yeast, algal or a fish cell. The animal cell may be mammalian, insect, bovine, primate, or a pluripotent stem cell. In one aspect, the animal cell may be a mammalian cell; and the mammalian cell may be keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, 1-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C$_3$H/IOTI/2 cells, HSDM$_1$C$_3$ cells, KLN$_2$O$_5$ cells, McCoy cells, Mouse L cells, Strain 2071 (Mouse L) cells, L-M strain (Mouse L) cells, L-MTK$^-$ (Mouse L) cells, NCTC clones 2472 and 2555, SCC-PSA1 cells, Swiss/3T3 cells, Indian muntjac cells, SIRC cells, C$_{II}$ cells, and Jensen cells, Sp2/0, NS0, NS1 cells or engineered cells thereof. In one aspect, the mammalian cell may be a CHO cell.

In all aspects of the methods used herein, the cells may produce an immunoglobulin or a fragment thereof; and the cell may produce greater than 3000 mg/L of immunoglobulin or a fragment thereof.

Alternately, in all aspects of the methods used herein, the cells may produce a virus or a virus-like particle (VLP); and the virus may be a recombinant virus. The virus may be but is not limited to an adenovirus, lentivirus, baculovirus, sendai virus, vaccinia virus, or an engineered viral derivative thereof. In the aspects described herein, the VLP may carry a nucleic acid, or it may carry a RNA.

In yet another aspect, the present invention is also directed to a method of preparing a cell culture medium, concentrated feed or cell culture supplement, comprising combining one or more small peptides with a carbohydrate and at least one amino acid or salt thereof, wherein each of the one or more small peptides comprises a cysteine or a tyrosine. In one embodiment, the amino acids of the one or more small peptides, which are other than cysteine or tyrosine, (or referred to as the remaining amino acids) may be selected from the group consisting of alanine, glycine, serine, valine, proline, aspartic acid, arginine, glutamine or glutamic acid. In one preferred aspect, the amino acids other than cysteine or tyrosine, are alanine or glycine. In another set, the remaining amino acids may also be one or more of arginine, asparagine, aspartic acid, cysteine, glutamic acid, histidine, isoleucine, lysine, methionine, phenylalanine, proline, hydroxyproline, serine, threonine, tryptophan, tyrosine, and valine. In another preferred aspect of the above method, one or more dipeptides may be selected from X-tyrosine, X-cysteine, tyrosine-X, or cysteine-X, or a salt thereof, wherein X is selected from alanine, glycine, serine, valine, proline, aspartic acid, arginine or glutamic acid, and wherein the N-terminal amino acid of the one or more dipeptide has a free amino group. In a most preferred aspect, X is alanine or glycine. In a most preferred aspect, the carbohydrate may be glucose. Additionally, the cell culture medium may further comprise a vitamin, a salt, a buffering agent, or an inorganic element; or, may not contain a lipid, a hydrolysate or a fraction thereof, or a growth factor; or may not contain a protein; or, the cell culture medium may be concentrated as a 2× or greater formulation; or, the one or more dipeptides may be alanyl tyrosine and/or alanyl cysteine; or, the one or more dipeptides are present in the cell culture medium at a concentration of about 1 g/L to about 16 g/L; or preferably, the one or more dipeptides are present at a concentration of about 2.5 g/L to about 8.5 g/L. In most aspects, the cell culture medium stored at 2-8° C. remains free of precipitate for over 12 months.

The present invention is also directed to a method for analyzing a cell culture medium, concentrated feed, or reconstituted medium, the method comprising determining the presence or absence of a short peptide comprising cysteine or tyrosine in the medium. In one aspect, the cell culture medium, concentrated feed, or reconstituted medium may be serum-free, protein-free, hydrolysate-free, and the analyzing may be performed by, but may not be limited to, mass spectrometry (LCMS); capillary electrophoresis and HPLC.

The invention is also directed to a composition comprising the cell culture medium, concentrated feed, or reconstituted medium described above and a cell.

The invention is also directed to a method of making a recombinant protein in a cell culture medium comprising: contacting a cell with the cell culture medium, concentrated feed, or reconstituted medium described above; and cultivating said cell under conditions suitable for the growth of said cell and/or the expression of said recombinant protein.

The invention is also directed to a kit for the cultivation of a cell in vitro, said kit comprising one or more containers, wherein a first container contains a medium comprising at least one dipeptide described above, and wherein said medium supports the growth of the cell in culture and/or the expression of recombinant protein. The culturing of the cell may be in suspension or in adherent culture. The growth may be high-density growth.

The invention is also directed to a method of making a virus or a viral particle in a cell culture medium, concentrated feed, or reconstituted medium described above comprising: culturing a recombinant cell in the cell culture medium described above, wherein the medium supports the growth of said cell under conditions suitable for expression of said virus or viral particle.

The invention is also directed to a recombinant protein produced by the methods described above; or, the virus or viral particle produced by the methods described above; or, the use of a cell culture medium, concentrated feed, or reconstituted medium described above, to produce a virus or a recombinant protein; or, a culture medium, concentrated feed, or reconstituted medium produced by the methods described above.

BRIEF DESCRIPTION OF THE DRAWINGS

The accompanying drawings, which are incorporated in and constitute a part of this specification, illustrate certain embodiments of the invention, and together with the written description, serve to explain certain principles of the invention.

DETAILED DESCRIPTION

Figure 1:
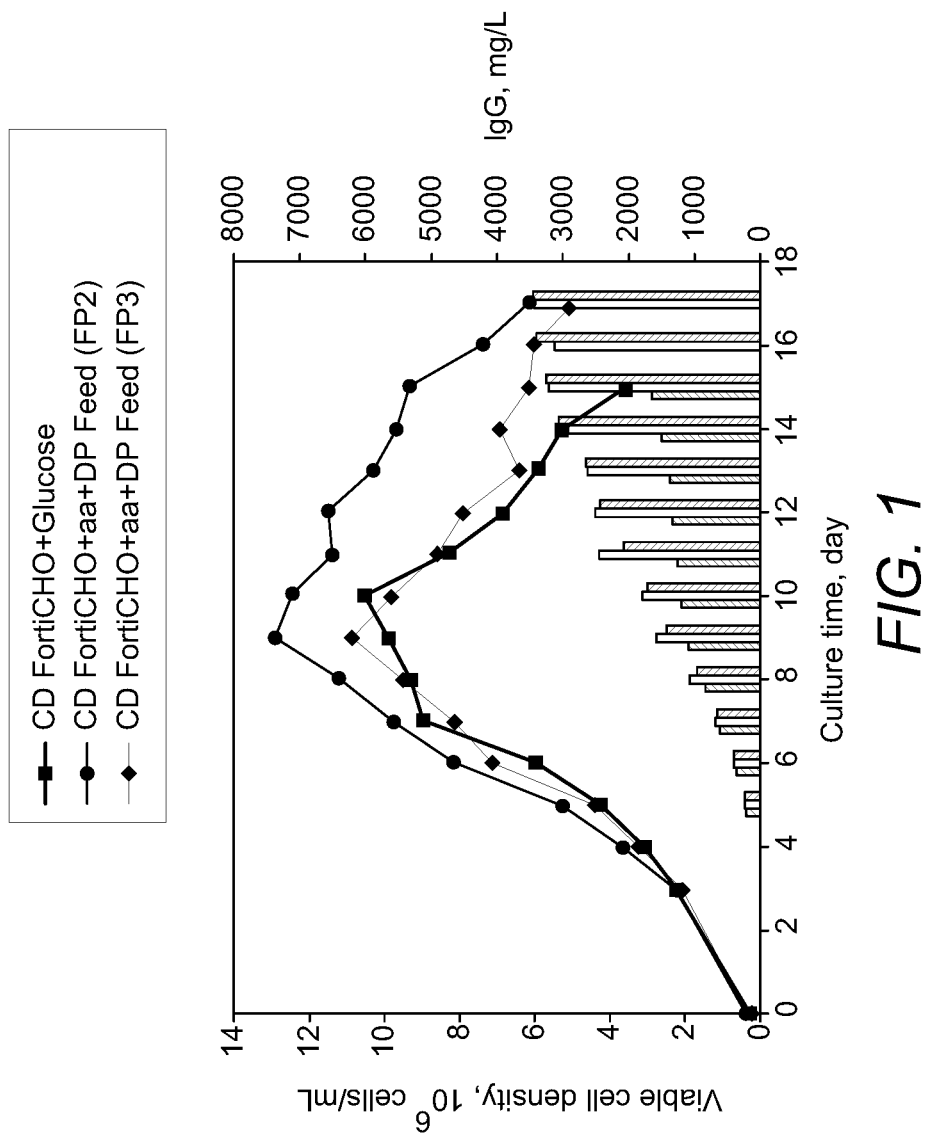
FIG. 1 shows viable cell density (×10$^6$ cells/mL) (depicted by curves), and IgG titer (mg/L) (depicted by bars) of CHO cells grown in (i) a basal cell culture medium (CD FortiCHO™) supplemented with either a glucose feed, and (ii) CD FortiCHO™+aa (concentrated amino acid mixture with low levels of cysteine and tyrosine, with glucose)+DP (dipeptide) feed schedule 2 (FP2) or (iii) CD FortiCHO™+aa (concentrated amino acid mixture with low levels of cysteine and tyrosine, with glucose)+DP (dipeptide) feed schedule 3 (FP3). See Examples.

Reference will now be made in detail to various exemplary embodiments. It is to be understood that the following detailed description is provided to give the reader a fuller understanding of certain embodiments, features, and details of aspects of the invention, and should not be interpreted as a limitation of the scope of the invention.

1. Definitions

In order that the present invention may be more readily understood, certain terms are first defined. Additional definitions are set forth throughout the detailed description.

As used herein, "cell culture" or "culture" refers to the maintenance of cells in an artificial (e.g., an in vitro) environment. It is to be understood, however, that the term "cell culture" is a generic term and may be used to encompass the cultivation not only of individual prokaryotic (e.g., bacterial) or eukaryotic (e.g., animal, plant and fungal) cells, but also of tissues, organs, organ systems or whole organisms, for which the terms "tissue culture," "organ culture," "organ system culture" or "organotypic culture" may occasionally be used interchangeably with the term "cell culture."

As used herein, "cultivation" refers to the maintenance of cells in an artificial environment under conditions favoring growth, differentiation, or continued viability, in an active or quiescent state, of the cells. Thus, "cultivation" may be used interchangeably with "cell culture" or any of its synonyms described above.

As used herein, "cell culture medium," "culture medium," or "medium" (and in each case plural media) refer to a nutritive composition that supports the cultivation and/or growth of cells. The cell culture medium may be a complete formulation, i.e., a cell culture medium that requires no supplementation to culture cells, may be an incomplete formulation, i.e., a cell culture medium that requires supplementation or may be a medium that may supplement an incomplete formulation or in the case of a complete formulation, may improve culture or culture results. The terms "cell culture medium," "culture medium," or "medium" (and in each case plural media) refer to unconditioned cell culture media that has not been incubated with cells, unless indicated otherwise from the context. As such, the terms "cell culture medium," "culture medium," or "medium" (and in each case plural media) are distinguished from "spent" or "conditioned" medium, which may contain many of the original components of the medium, as well as a variety of cellular metabolites and secreted proteins.

As used herein, "small peptide" refers to a chain of two to six amino acids joined together by one or more peptide or equivalent bonds, wherein at least one of the amino acids is a tyrosine or a cysteine. Preferably the amino acids in the small peptide, other than tyrosine or cysteine, exhibit good solubility properties at neutral pH. Thus, in one embodiment, the amino acids in the small peptide, other than tyrosine or cysteine, are selected from alanine, glycine, serine, valine, proline, glutamic acid, aspartic acid, glutamine, and arginine. In another embodiment, the N-terminal amino acid of the small peptide has a free amino group. In an embodiment of the invention, the small peptide may comprise a non-amino acid with a free amine group, like ethanolamine, or a free carboxylic group, or a similar compound.

As used herein, "extract" refers to a composition comprising a component of a substance or a concentrated preparation of the subgroups of a substance, typically formed by treatment of the substance either mechanically (e.g., by pressure treatment) or chemically (e.g., by distillation, precipitation, enzymatic action or high salt treatment).

As used herein, the term "ingredient" refers to any compound, whether of chemical or biological origin, that can be used in cell culture media to maintain or promote the growth of proliferation of cells. The terms "component," "nutrient" and "ingredient" can be used interchangeably and are all meant to refer to such compounds. Typical ingredients that can be used in cell culture media include amino acids, salts, metals, sugars, carbohydrates, lipids, nucleic acids, hormones, vitamins, fatty acids, proteins and the like. Other ingredients that promote or maintain cultivation of cells ex vivo can be selected by those of skill in the art, in accordance with the particular need.

A "1× formulation" refers to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See Cell Culture Technology for Pharmaceutical and Cell-Based Therapies, 42-50 (Sadettin Ozturk and Wei-Shou Hu eds., Taylor and Francis Group 2006), which is incorporated by reference herein in its entirety. The osmolality and/or pH, however, may differ in a 1× formulation compared to the culture medium, particularly when fewer ingredients are contained in the 1× formulation.

A "10× formulation" is meant to refer to a solution wherein each ingredient in that solution is about 10 times more concentrated than the same ingredient in the cell culture medium. For example, a 10× formulation of RPMI-1640 culture medium may contain, among other ingredients, 2.0 g/L L-arginine, 0.5 g/L L-asparagine, and 0.2 g/L L-aspartic acid (compare 1× formulation, above). A "10× formulation" may contain a number of additional ingredients at a concentration about 10 times that found in the 1× culture medium. As will be readily apparent, "5× formulation," "25× formulation," "50× formulation," "100× formulation," "500× formulation," and "1000× formulation" designate solutions that contain ingredients at about 5-25-, 50-, 100-, 500-, or 1000-fold concentrations, respectively, as compared to a 1× cell culture medium. Again, the osmolality and pH of the media formulation and concentrated solution may vary. A formulation may contain components or ingredients at 1× with respect to a particular cell culture protocol, but at a concentration, for example, 2, 2.5, 5, 6.7, 9, 12 etc. X with respect to a different culture protocol or different base medium.

A dimer consists of two dipeptides. So, for e.g., a dimer of Ala-Cys would comprise Ala-Cys-Cys-Ala, wherein the cys-cys are bonded by a disulfide linkage. Ala-Cys-Cys-Ala could also be referred to as N,N'-di-L-Alanyl-L-Cystine.

1. Small Peptides

The present disclosure concerns the use of small peptides, including dipeptides, in cell culture medium. Applicants have found that preparing cell culture medium containing the desired concentrations of certain amino acids, such as tyrosine and cysteine, has not been possible due to the low solubility of tyrosine and low stability of cysteine. The solubility and stability problems of tyrosine and cysteine have been addressed by using less than the desired concentration of tyrosine or cysteine in the aqueous cell culture medium, thereby making them the rate limiting amino acids for optimal cell growth and/or protein production, as nutrients are used during cell culture. Although using less than the desired concentration of tyrosine and cysteine may result in an acceptable aqueous shelf life, solubility and stability, it may also require the addition of higher volumes of media during cell culture supplementation, for e.g., in a fed-batch culture system to achieve desired productivity. This is undesirable, as the stoichiometric balance, pH and/or osmolality of the system would need to be re-adjusted as well.

The problem with large volume supplementation can be addressed by using a concentrated feed supplement. A desirable concentrated feed supplement is a nutritionally complex, stoichiometrically balanced nutrient additive that supplements nutrient-depleted culture systems, in a fed-batch culture system, which additionally, and desirably, may have auto-pH and auto-osmolality balancing characteristics. However, due to the low solubility of tyrosine and low stability of cysteine, concentrated feed compositions with high levels of cysteine and tyrosine have been a challenge to prepare. It generally results in the cysteine or tyrosine coming out of solution over time. Single part, pH-neutral, chemically-defined concentrated feeds that are stable have thus been difficult to synthesize. To circumvent the problem, multi-part concentrated feeds that are acidic or alkaline have been prepared.

Applicants have discovered that it is possible to substitute the free amino acids, tyrosine and cysteine, in a cell culture medium with small peptides like dipeptides alanyl-tyrosine, glycyl-tyrosine, alanyl-cysteine (which forms a disulfide dimer, [AlaCys]$_2$), or glycyl-cysteine (which forms a disulfide dimer, [GlyCys]$_2$), or other small peptides comprising one or more tyrosines or cysteines. Cell culture medium containing these dipeptides, or other small peptides, provides cells with concentrations of tyrosine and/or cysteine sufficient to support maximal cell growth and/or protein production while avoiding the solubility and stability problems associated with free tyrosine and/or cysteine.

The small peptides of the invention have two to six amino acids, wherein at least one of the amino acids is a cysteine or tyrosine, and where the remaining amino acids can be any amino acid. Preferably the amino acids in the small peptide, other than tyrosine or cysteine, exhibit good solubility properties at neutral pH. In one embodiment, the amino acids in the small peptide other than tyrosine or cysteine are selected from alanine, glycine, serine, valine, proline, glutamic acid, or aspartic acid. In another embodiment, the N-terminal amino acid of the small peptide has a free amino group. In an embodiment of the invention, the small peptide (di, tri, four, five or six amino acids) may comprise a non-amino acid with a free amine group, like ethanolamine, or a free carboxylic group, or a similar compound that can contribute to a peptide bond. In another embodiment, the small peptide may comprise cysteine dimerized via the sulfide bond. Due to cysteine-cysteine dimerization (cys-cys) dimerization, although the small peptides of the invention are defined as having a length of 2 to 6 amino acids, there may be compositions that result in longer peptides due to spontaneous cysteine-cysteine dimerization that may occur within a media or feed of the invention. Such compounds are also soluble, even in high concentrations, and as such, are completely within the scope of this invention.

In other embodiments, the small peptides are dipeptides having two amino acids and represented by the formula: X-tyrosine, X-cysteine, tyrosine-X, or cysteine-X, or a salt thereof, wherein X is any amino acid, and wherein the N-terminal amino acid of the dipeptide has a free amino group. Thus, the dipeptides are distinct from the N-acyl dipeptides disclosed in U.S. Pat. No. 5,534,538, which require an acyl group covalently bonded to the amino group of the N-terminal amino acid. According to U.S. Pat. No. 5,534,538, it is the presence of the acyl group that confers the superior stability properties to the dipeptides. Preferably, X is an amino acid with good solubility properties. In one embodiment, X is alanine or glycine. In another embodiment, X is serine, valine, proline, glutamic acid, or aspartic acid.

In one embodiment, the small peptides are dipeptides having two amino acids, and the one or more dipeptides of the invention are selected from X-tyrosine, X-cysteine, tyrosine-X, and cysteine-X, or a salt thereof, wherein X is any amino acid, and wherein the N-terminal amino acid of the dipeptide has a free amino group. In one embodiment, X is alanine or glycine. In another embodiment, X is any amino acid, derivative of an amino acid, a non-amino acid that has an amino-group, like ethanolamine. In an aspect of this embodiment, the preferred amino acid is selected from the group: serine, valine, proline, aspartic acid, arginine, glutamine, or glutamic acid.

In another embodiment, the small peptides are tripeptides having three amino acids, including the following tripeptides: X-X-tyrosine, X-X-cysteine, X-tyrosine-X, X-cysteine-X, tyrosine-X-X, cysteine-X-X, or a salt thereof, wherein X is any amino acid. In one embodiment, the N-terminal amino acid of the tripeptide has a free amino group. Preferably, X is an amino acid with good solubility properties. In one embodiment, X is alanine or glycine. In another embodiment, X is serine, valine, proline, glutamic acid, glutamine, arginine, or aspartic acid. In a certain aspect of the invention, the compositions described above that containing cysteine and tyrosine in small peptides is used to increase protein production in a cell line. In a preferred aspect of the invention, the increased protein is an antibody that is produced in higher titers than in media without the small peptides. By higher antibody production is meant about 0.1 g/L to about 10 g/L, about 0.1 g/L to about 5 g/L, about 0.1 g/L to about 2.5 g/L, about 0.1 g/L to about 1 g/L, preferably about 1 g/L to about 10 g/L, more preferably about 2 g/L to about 8 g/L, and so on.

Depending on the cell and the intended use of the cell, one or more small peptides or dipeptides of the cell culture medium, feed, concentrated media or feed, etc. will optimally be present at concentrations stoichiometrically balanced to optimize cell culture performance. For example, the concentration of one or more small peptides or dipeptides in some cell culture media or the concentrated feeds may be at about 0.5 g/L to about 30 g/L, about 0.5 g/L to about 25 g/L, about 0.5 g/L to about 20 g/L, about 0.5 g/L to about 16 g/L, about 0.5 g/L to about 10 g/L, about 0.5 g/L to about 5 g/L, about 0.5 g/L to about 4 g/L, about 1 g/L to about 30 g/L, about 1 g/L to about 20 g/L, about 1 g/L to about 16 g/L, about 1 g/L to about 10 g/L, about 1 g/L to about 5 g/L, about 2.5 g/L to about 30 g/L, about 2.5 g/L to about 20 g/L, about 2.5 g/L to about 16 g/L, about 2.5 g/L to about 10 g/L, about 2.5 g/L to about 5 g/L, or about 2.5 g/L to about 4.5 g/L, about 5 g/L to about 30 g/L, about 5 g/L to about 25 g/L, about 5 g/L to about 20 g/L, about 5 g/L to about 16 g/L, about 5 g/L to about 10 g/L, about 5 g/L to about 5 g/L, about 5 g/L to about 4 g/L, and so on. In some media formulations or prototype media formulations, one or more small peptides, and/or one or more dipeptides may be present at a concentration of about 2.5 g/L to about 8.5 g/L in the media or prototype media. Additionally, some embodiments of the invention provide methods of preparing "auto-pH media" or feed powders which automatically are at a desired pH upon rehydration/reconstitution with a solvent. In accordance with the invention, such media or feeds may be in powdered (dry powder (DPM), advanced powder (APM) or advanced granulating technology (AGT) or in liquid form.

Animal cell culture media or feeds prepared by the present methods will, upon reconstitution, preferably have a pH of about 6-8, or about 7-8, or about 6.0-6.3 (for insect cells), more preferably about 7-7.5 or about 7.2-7.4, most preferably around 7.0; and plant cell culture media or feeds prepared by the present methods will, upon reconstitution, preferably have a pH of about 4-8, preferably about 4.5-7, 5-6 or 5.5-6, or preferably about 6.0 to 6.3. Of course, optimal pH for a given culture medium to be used on a particular cell type may also be determined empirically by one of ordinary skill using art-known methods.

2. Cell Culture Medium

A cell culture medium is composed of a number of ingredients and these ingredients vary from one culture medium to another. As noted above, a cell culture medium may be a complete formulation, i.e., a cell culture medium that requires no supplementation to culture cells, may be an incomplete formulation, i.e., a cell culture medium that requires supplementation or may be a supplement that may supplement an incomplete formulation or in the case of a complete formulation, may improve culture or culture results.

Generally a cell culture medium will have solutes dissolved in solvent. The solutes provide an osmotic force to balance the osmotic pressure across the cell membrane (or wall). Additionally the solutes will provide nutrients for the cell. Some nutrients will be chemical fuel for cellular operations; some nutrients may be raw materials for the cell to use in anabolism; some nutrients may be machinery, such as enzymes or carriers that facilitate cellular metabolism; some nutrients may be binding agents that bind and buffer ingredients for cell use or that bind or sequester deleterious cell products.

Depending on the cell and the intended use of the cell, the ingredients of the cell culture medium will optimally be present at concentrations balanced to optimize cell culture performance. Performance will be measured in accordance with a one or more desired characteristics, for example, cell number, cell mass, cell density, $O_2$ consumption, consumption of a culture ingredient, such as glucose or a nucleotide, production of a biomolecule, secretion of a biomolecule, formation of a waste product or by product, e.g., a metabolite, activity on an indicator or signal molecule, etc. Each or a selection of the ingredients will thus preferably optimized to a working concentration for the intended purpose.

Culture media or feed supplements of the invention may be available in a dry format that requires only addition of a solvent such as water. Preferably the dry format powder is prepared by at least one method selected from the group consisting of milling, impacting, extruding and cutting or breaking, wet granulation, high shear granulation, pan granulation and fluidized bed agglomeration. Dry formats include, but are not limited to, dry powder format (DPM), agglomerated (AGT™) format, advanced powder media (APM), or other suitable dry formats. Preferably, once water is added, dissolution should occur quickly and the resultant liquid can be filtered and added directly to the cells without any pH adjustment. The reconstituted medium or concentrated supplement may be prepared in variable bulk quantities and is amenable to sterilization, particularly by ionizing or ultraviolet irradiation.

a. Carbohydrates

Cell culture medium ingredients typically include a carbohydrate, amino acids, salts, trace elements, and vitamins. For mammalian cells, the main carbohydrate used in cell culture media is glucose, routinely supplemented at 5 to 25 nM. See Cell Culture Technology for Pharmaceutical and Cell-Based Therapies, 51 (Sadettin Ozturk and Wei-Shou Hu eds., Taylor and Francis Group 2006). In addition to glucose, any hexose like galactose, fructose, or mannose or a combination of these may be used. In addition, mammalian cells can also use glutamine as a major energy source. Glutamine is often included at higher concentrations than other amino acids (2-8 mM). However, as noted above, glutamine can spontaneously break down to form ammonia and certain cell lines produce ammonia faster, which is toxic. Therefore, glutamate and glutamine dipeptides have been used as substitutes for glutamine to reduce the build up of toxic ammonia in the cell culture medium.

b. Amino Acids

Amino acids are important in cell culture medium for maintaining the metabolic function of the cultured cells. Cell culture medium typically includes the essential amino acids (i.e., those amino acids that are normally not synthesized in vivo by mammals) as well as certain non-essential amino acids. A non essential amino acid is typically included in the cell culture medium if the cell line is not capable of synthesizing the amino acid or if the cell line cannot produce sufficient quantities of the amino acid to support maximal growth. Exemplary amino acids include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-hydroxyproline, L-serine, L-threonine, L-tryptophan, L-tyrosine, and L-valine.

c. Salts

Salts are added to cell culture medium to maintain isotonic conditions and prevent osmotic imbalances. The osmolality of standard mammalian cell culture medium is about 300 mOsm/kg, although many cell lines can tolerate an approximately 10% variation of this value. The osmolality of some insect cell cultures tend to be higher than 300 mOsm/kg, and this may be 0.5%, 1%, 2 to 5%, 5-10%, 10-15%, 15-20%, 20-25%, 25-30% higher than 300 mOsm/kg. The most commonly used salts in cell culture medium include $Na^+$, $K^+$, $Mg^{2+}$, $Ca^{2+}$, $Cl^-$, $SO_4^{2-}$, $PO_4^{3-}$, and $HCO_3^-$ (e.g., $CaCl_2$), KCl, NaCl, $NaHCO_3$, $Na_2HPO_4$). Therefore, the desired osmolality for a cell culture medium for cultivation of a particular cell type may also be determined empirically by one of ordinary skill in the art, using art-known methods.

d. Inorganic Elements

Other inorganic elements that are present in serum in trace amounts can be included in cell culture medium, as described in US 2005/0287666, which is hereby incorporated by reference in its entirety. They include Mn, Cu, Zn, Mo, Va, Se, Fe, Ca, Mg, Si, and Ni. Other inorganic elements that have been added to cell culture medium, although not as frequently, include Al, Ag, Ba, Br, Cd, Co, Cr, F, Ge, J, Rb, and Zr. Many of these elements are involved in enzymatic activity. They may be provided in the form of salts such as $CaCl_2$), $Fe(N03)_3$, $MgCl_2$, $MgSO_4$, $MnCl_2$, NaCl, NaHCO3, Na2HPO4, and ions of the trace elements, such as, selenium, vanadium and zinc. These trace elements may be provided in a variety of forms, preferably in the form of salts such as $Na_2SeO_3$, $NH_4VO_3$, etc. These inorganic salts and trace elements may be obtained commercially, for example from Sigma (Saint Louis, Mo.).

e. Vitamins

Vitamins are typically used by cells as cofactors. The vitamin requirements of each cell line vary greatly, although generally extra vitamins are needed if the cell culture medium contains little or no serum or if the cells are grown at high density. Exemplary vitamins include biotin, choline chloride, folic acid, i-inositol, nicotinamide, D-$Ca^{++}$-pantothenate, pyridoxal, riboflavin, thiamine, pyridoxine, niacinamide, A, $B_6$, $B_{12}$, C, $D_3$, E, K, and p-aminobenzoic acid (PABA).

f. Serum

Serum, the supernatant of clotted blood, can be used in cell culture medium to provide components that promote cell growth and/or productivity. These serum components include attachment factors, micronutrients (e.g., trace elements), growth factors (e.g., hormones, proteases), and protective elements (e.g., antitoxins, antioxidants, antiproteases). Serum is available from a variety of animal sources including bovine or equine. When included in cell culture medium, serum is typically added at a concentration of 5-10%. Certain cell culture media are serum free.

g. Growth Factors

To promote cell growth in the absence or serum or in serum reduced media, one or more of the following polypeptides can be added to a cell culture medium: for example, fibroblast growth factor (FGF), including acidic FGF and basic FGF, insulin, insulin-like growth factor (IGF), epithelial growth factor (EGF), nerve growth factor (NGF), platelet-derived growth factor (PDGF), and transforming growth factor (TGF), including TGFα and TGFβ, any cytokine, such as interleukins 1, 2, 6, granulocyte stimulating factor, Leukocyte inhibitory factor (LIF), etc.

In certain embodiments, the cell culture medium does not contain a growth factor. In protein-free media, insulin may be replaced with zinc or a zinc containing compound, as described in WO 98/08934, which is hereby incorporated by reference in its entirety.

h. Lipids

One or more lipids can also be added to a cell culture medium. Serum typically contains lipids, such as fatty acids (e.g., linoleic acid, linolenic acid, arachidonic acid, palmitoleic acid, oleic acid, polyenoic acid, and/or fatty acids of 12, 14, 16, 18, 20, or 24 carbon atoms, each carbon atom branched or unbranched), phospholipids, lecithin (phophatidylcholine), and cholesterol. Alternatively, one or more of these lipids can be included as supplements in serum-free media. Phosphatidic acid and lysophosphatidic acid stimulate the growth of certain anchorage-dependent cells, such as MDCK, mouse epithelial, and other kidney cell lines, while phosphatidylcholine, phosphatidylethanolamine, and phosphatidylinositol stimulate the growth of human fibroblasts in serum-free media. Ethanolamine and cholesterol have also been shown to promote the growth of certain cell lines. In certain embodiment, the cell culture medium does not contain a lipid.

i. Carrier Proteins

One or more carrier proteins, such as bovine serum albumin (BSA) or transferrin, can also be added to the cell culture medium. Carrier proteins can help in the transport of certain nutrients or trace elements. BSA is typically used as a carrier of lipids, such as linoleic and oleic acids, which are insoluble in aqueous solution. In addition, BSA can also serve as a carrier for certain metals, such as Fe, Cu, and Ni. In protein-free formulations, non-animal derived substitutes for BSA, such as cyclodextrin, can be used as lipid carriers. Transferrin is involved in transporting iron across cell membranes. In certain cases, human serum albumin may be necessary for the cultivation of cells (for. e.g., such as in xeno-free (XF) culture) desirable for products generated for downstream therapeutic use. In other instances, recombinant human serum albumin may be used in the cell culture medium for the cultivation of cells. In particular cases, the recombinant human serum albumin may be derived from plant, algal or fungal sources such as rice, corn, potato, wheat, even yeast, etc. to provide for animal-origin free (AOF) culturing of cells. In protein-free formulations, transferrin can be replaced by ferric and/or ferrous salts, as described in WO 98/08934, which is hereby incorporated by reference in its entirety, or a hydroxypyridine derivative, as described in US 2007/0254358, which is hereby incorporated by reference in its entirety. Additionally, in protein-free formulations, insulin can be replaced by zinc, vanadium or other suitable divalent salts.

j. Attachments Proteins

One or more attachment proteins, such as fibronectin, laminin, and pronectin, can also be added to a cell culture medium to help promote the attachment of anchorage-dependent cells to a substrate.

k. Buffering Agent

The cell culture medium can optionally include one or more buffering agents. Suitable buffering agents include, but are not limited to, N-[2-hydroxyethyl]-piperazine-N'-[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

l. Polyanionic or Polycationic Compounds

Polyanionic or polycationic compounds can prevent the cells from clumping and promote growth of the cells in suspension. See WO 98/08934, which is hereby incorporated by reference in its entirety. Exemplary polyanionic compounds include polysulfonated or polysulfated compound, such as, heparin, dextran sulfate, heparan sulfate, dermatan sulfate, chondroitin sulfate, pentosan polysulfate, a proteoglycan or the like.

In addition to the small peptides or dipeptides described herein, the cell culture medium comprises one or more ingredients, such as those listed above. In one embodiment, the cell culture medium comprises one or more small peptides or one or more dipeptides, as described herein, and optionally comprises one or more of the following ingredients: ethanolamine, D-glucose, HEPES, insulin, a cytokine (e.g., IL-6), heparin, dextran sulfate, linoleic acid, lipoic acid, phenol red, PLURONIC® F68, putrescine, sodium pyruvate, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-$Ca^{++}$-pantothenate, folic acid, i-inositol, niacinamide, pyridoxine, riboflavin, thiamine, vitamin $B_{12}$, one or more calcium salts, $Fe(NO_3)_3$, KCl, one or more magnesium salts, one or more manganese salts, NaCl, $NaHCO_3$, $Na_2HPO_4$, one or more selenium salts, one or more vanadium salts and one or more zinc salts. In one embodiment, the one or more dipeptides are selected from X-tyrosine, X-cysteine, tyrosine-X, and cysteine-X, or a salt thereof, wherein X is any amino acid, and wherein the N-terminal amino acid of the dipeptide has a free amino group. In one embodiment, X is alanine or glycine. In another embodiment X is serine, valine, proline, aspartic acid, or glutamic acid.

The media described herein can be a 1× formulation or can be concentrated as anything greater than a 1× formulation, for example, as a 2×, 5×, 10×, 20×, 50×, 500×, or 1000× medium formulation as the solubilities of the individual components allow. If the individual medium ingredients are prepared as separate concentrated solutions, an appropriate (sufficient) amount of each concentrate is combined with a diluent to produce a 1× medium formulation. Typically, the diluent used is water but other solutions including aqueous buffers, aqueous saline solution, or other aqueous solutions may be used.

The media described herein can also be prepared in different forms, such as dry powder media, a granulated preparation (which requires addition of water, but not other processing, such as pHing), liquid media or as media concentrates.

3. Serum-Free Medium

Potential problems associated with serum, including batch to batch variation, high protein content, risk of contaminants (e.g., viruses, mycoplasma, prions), limited availability, and high cost, have driven the production of serum-free media. Furthermore, improved levels of recombinant protein expression can be obtained from cells grown in serum-free medium, relative to the level of expression seen in cells grown in medium supplemented with serum (Battista, P. J. et al., Am. Biotech Lab. 12: 64-68 (1994)).

In these serum-free media, serum can be replaced with a defined hormone, or hormone cocktails, such as HITES or ITES, which contain hydrocortisone, insulin, transferrin, ethanolamine, and selenite. Alternatively, the serum-free media can contain growth factor extracts from endocrine glands, such as epidermal or fibroblast growth factors. Serum-free media can also contain other components as a substitute for serum, including purified proteins (animal or recombinant), peptones, amino acids, inorganic salts, and animal or plant hydrolysates (or fractions thereof).

Serum-free media may be chemically defined or undefined. In chemically defined media, the identity of the components and their amounts are known, whereas the opposite is true for chemically undefined media. Chemically defined media, therefore, are designed, in part, to reduce the risk of contaminants and to reduce batch to batch variation. Chemically defined supplements that can be added to cell culture media include growth factors, hormones, carrier proteins, and/or attachment factors. In a preferred embodiment, the basal medium used with the media or feeds comprising small peptides is a chemically-defined medium. In another preferred embodiment, the concentrated cell culture media or concentrated feed of the invention comprising small peptides is also a chemically-defined composition. In yet another preferred embodiment, the concentrated feed or medium of the invention comprising small peptides including cysteine and tyrosine is a single part feed and is chemically-defined. In another aspect, all the above compositions comprising small peptides including cysteine and tyrosine are auto-pH and auto-osmolality balanced. In yet another aspect, all the above compositions comprising small peptides including cysteine and tyrosine are stoichiometrically balanced.

4. Protein-Free Media

Serum-free media contains reduced amounts of protein as compared to cell culture media containing serum. However, serum-free media may still contain one or more of a variety of animal-derived components, including albumin, fetuin, various hormones and other proteins. The presence of proteins makes purification of recombinant protein difficult, time-consuming, and expensive and can also lead to reduced product yields and/or purity. Thus, in one embodiment, the cell culture medium is protein free.

Protein-free media can be obtained by methods known in the art, such as by removing any remaining proteins from serum-free media. While the removal of such proteins from the cell culture media can impair the media's ability to support cell growth, other components can be added to the media to mitigate the effect of removing the proteins from the media. For example, as discussed above, cyclodextrin can replace BSA and iron salts or a hydroxypyridine derivative can replace transferrin. In other cases, animal tissue or plant hydrolysates (or fractions thereof) have been used to supplement protein-free media.

5. Fed-Batch Cultivation

Fed-batch cultivation of cells is typically used for industrial production of biomolecules, such as proteins, to increase cell concentration and to extend culture lifetime for a high product concentration and volumetric productivity. Fed-batch cultures involve the controlled addition of one or more nutrients, in the form of feeds which may contain nutrients that are quickly utilized by cells such as glucose, amino acids to a basal medium. The nutrient(s) help to control the growth of the cell culture by attempting to prevent nutrient depletion and byproduct accumulation, important parameters, such as pH, osmolality and $CO_2$ concentration, within levels that promote cell growth or minimize cell death for optimal product expression. See Cell Culture Technology for Pharmaceutical and Cell-Based Therapies, 349-386 (Sadettin Ozturk and Wei-Shou Hu eds., Taylor and Francis Group 2006). Even then, fed batch cultures often result in high concentrations of inhibitory metabolites and high osmolalities that eventually are incompatible with cell viability.

A basal medium is typically used for maintenance of a cell culture, and can comprise a number of ingredients, including amino acids, vitamins, organic and inorganic salts, sugars and other components, each ingredient being present in an amount which supports the cultivation of the cell in vitro. Basal media useful for prokaryotic cell culture including bacterial and archebacterial cultures, viral cultures, plant cell culture, insect cell culture, mammalian cell culture can be used with the small peptide Examples of basal media include Eagle's basal medium (BME), Eagle's minimal essential medium (EMEM), Dulbecco's modification of Eagle's medium (DMEM), Glasgow's modification of Eagle's medium (GMEM), Joklik's modified Eagle's medium, Alpha modified Eagle's medium, Roswell Park Memorial Institute (RPMI) medium, Fischer's medium, Leibovitz L-15 medium, Trowell's T-8 medium, Williams' medium E, Biggers' medium, Connaught Medical Research Laboratories (CMRL) 1066 medium, Ham's F10 medium, Ham's F12 medium, Iscove's modified Dulbecco's medium (IMDM), MCDB 104, MCDB 110, MCDB 153, Medium 199, NCTC 135 medium, and Waymouth's medium MB 752/1. For CHO cells, preferred basal media include CD CHO, CD OptiCHO™, and CD FortiCHO™ (all from Life Technologies, Corp., Carlsbad, Calif.). Preferred concentrated feed supplements for CHO cells include, but are not limited to, CHO CD EfficientFeed™ A (Invitrogen Cat. No. A1023401), CHO CD EfficientFeed™ B (Invitrogen Cat. No. A1024001), CHO CD EfficientFeed™ kit (Invitrogen Cat. No. A1024101), CD EfficientFeed™ C AGT™ (Invitrogen Cat. No. A1327501, Life Technologies Corp., Carlsbad, Calif.).

In fed-batch cultivation, cells are typically grown up to a certain time point in batch mode using a basal medium. Subsequently, a medium supplement (concentrated feed) comprising concentrated solutions of a single or multiple nutrients is added to provide nutrients, while minimizing volume increase or culture dilution. When the medium supplement is added to basal medium, it improves cell culture, as exhibited, for example, by more rapid cell growth, decreased doubling time, higher achievable density of cells, or higher production or yield of biomolecule, such as protein, e.g., antibody or other proteins of therapeutic interest.

A cell culture medium or concentrated feed of the invention, suitable for use in supplementing a basal medium, comprises one or more small peptides, including one or more dipeptides, as described herein. The cell culture medium or concentrated feed comprising cysteine and tyrosine may be optionally used in conjunction with another feed, say, a concentrated mixture of amino acids that may comprise one or more of the following ingredients: adenine, ethanolamine, a carbohydrate source (such as a hexose like either glucose, mannose, galactose, fructose, or even a combination thereof), heparin, a buffering agent, hydrocortisone, lipoic acid, phenol red, phosphoethanolamine, putrescine, sodium pyruvate, tri-iodothyronine, thymidine, L-alanine, L-arginine, L-asparagine, L-aspartic acid, L-cysteine, L-glutamic acid, L-glutamine, glycine, L-histidine, L-hydroxyproline, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, D-Ca'-pantothenate, folic acid, i-inositol, niacinamide, pyridoxine, riboflavin, thiamine, vitamin $B_{12}$, Pluronic F68, recombinant insulin, a calcium salt, $CuSO_4$, $FeSO_4$, $FeCl_3$, $Fe(NO_3)_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, $ZnCl_2$, $ZnSO_4$ or other zinc salts.

Thus, the concentrated mixture of amino acids used to supplement the basal medium may be made up of a stoichiometrically balanced mixture of amino acids, may or may not contain cysteine and tyrosine, and may optionally contain one or more of the following: a carbon source, vitamins, trace elements, and further, may be chemically-defined in that it does not contain any lipids, hydrolysates, or growth factors. In some instances, the concentrated mixture of amino acids may contain animal origin free hydrolysates or a fraction of a hydrolysate, for e.g., a plant hydrolysate. Any commercially available concentrated mixture of amino acids can be used, for instance, CHO CD EfficientFeed™ A (Invitrogen Cat. No. A1023401), CHO CD EfficientFeed™ B (Invitrogen Cat. No. A1024001), CHO CD EfficientFeed™ kit (Invitrogen Cat. No. A1024101), CD EfficientFeed™ C AGT™ (Invitrogen Cat. No. A1327501, Life Technologies Corp., Carlsbad, Calif.).

In one embodiment, the cysteine and tyrosine containing cell culture medium, or concentrated feed of the invention, suitable for use in supplementing a basal medium, is protein free. In another embodiment the cell culture medium, or concentrated feed of the invention suitable for use in supplementing a basal medium, is protein free and additionally does not contain lipids, hydrolysates or a fraction thereof, or growth factors, and therefore would be considered chemically-defined (CD). In one aspect of this embodiment, the cysteine and tyrosine containing cell culture medium, or concentrated feed of the invention may optionally contain one or more of the following: a carbon source, vitamins, trace elements, and further, may be chemically-defined in that it does not contain any lipids, hydrolysates, or growth factors.

6. Cells

Media containing the cysteine and tyrosine containing small peptides or dipeptides described herein can also be used to culture a variety of cells. Cells grown using the culture medium and feeds described herein can be derived from any prokaryote including archebacteria, algae, yeast, fungus, plant, insect, animal, preferably a mammal, and most preferably a mouse or a human. In one embodiment, the media is used to culture eukaryotic cells, including plant or animal cells, such as mammalian cells, fish cells, insect cells, amphibian cells or avian cells.

Mammalian cells that can be cultured with the media described herein include primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LS180 cells, LS174T cells, NCI-H-548 cells, RPMI 2650 cells, SW-13 cells, T24 cells, WI-28 VA13, 2RA cells, WISH cells, BS-C-I cells, LLC-$MK_2$ cells, Clone M-3 cells, 1-10 cells, RAG cells, TCMK-1 cells, Y-1 cells, LLC-$PK_1$ cells, PK(15) cells, $GH_1$ cells, $GH_3$ cells, L2 cells, LLC-RC 256 cells, $MH_1C_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, $MiCl_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, $HSDM_1C_3$ cells, $KLN_2O_5$ cells, McCoy cells, Mouse L cells, Strain 2071 (Mouse L) cells, L-M strain (Mouse L) cells, L-MTK⁻ (Mouse L) cells, NCTC clones 2472 and 2555, SCC-PSA1 cells, Swiss/3T3 cells, Indian muntjac cells, SIRC cells, $C_{II}$ cells, and Jensen cells, Sp2/0, NS0, NS1 cells or derivatives thereof).

Cells cultured according to the methods disclosed herein may be normal cells, diseased cells, transformed cells, mutant cells, somatic cells, genetically engineered cells, germ cells, stem cells, precursor cells or embryonic cells, any of which may be established or transformed cell lines or obtained from natural sources. Cells may be used for experimental purposes or for production of useful components. In certain cases, the cultivated cells themselves are the products and use of cells in cellular therapies. The cells may also be cultivated for protein production including antibody production, for small RNA production (like miRNA or siRNA), for virus or VLP (virus-like particle) production, generation and isolation of DNA or viral vectors, for nucleic acid production, for vitamin production, for desirable metabolites, biofuel synthesis, etc. In one embodiment, the media described herein is used to culture Chinese Hamster Ovary (CHO) cells. CHO cells have been classified as both epithelial and fibroblast cells derived from the Chinese hamster ovary. A cell line started from Chinese hamster ovary (CHO-K1) (Kao, F.-T. And Puck, T. T., Proc. Natl. Acad. Sci. USA 60: 1275-1281 (1968)) has been in culture for many years. Most biopharmaceuticals currently produce proteins in CHO cells for many advantages that the cell line has precise post-translation modification such as human-like glycosylation patterns, and low risk for transmission of human viruses.

7. Cultivation of Cells

Cells supported by the culture medium described herein can be cultivated according to the experimental conditions determined by the investigator. The examples below demonstrate at least one functional set of culture conditions useful for cultivation of certain mammalian cells. It is to be understood, however, that the optimal plating and culture conditions for a given animal cell type can be determined by one of ordinary skill in the art using only routine experimentation. For routine monolayer culture conditions, using the cell culture media described herein, cells can be plated onto the surface of culture vessels without attachment factors. Alternatively, the vessels can be precoated with natural, recombinant or synthetic attachment factors or peptide fragments (e. g., collagen, fibronectin, vitronectin, laminin and the like, or natural or synthetic fragments thereof), which are available commercially for example from Life Technologies, Corp. (Carlsbad, Calif.), R&D Systems, Inc. (Rochester, Minn.), Genzyme (Cambridge, Mass.) and Sigma (St. Louis, Mo.). Cells can also be seeded into or onto a natural or synthetic three-dimensional support matrix such as a preformed collagen gel or a synthetic biopolymeric material. For suspension cultivation, cells are typically suspended in the culture media described herein and introduced into a culture vessel that facilitates cultivation of the cells in suspension, such as a spinner flask, perfusion apparatus, or bioreactor. See Cell Culture Technology for Pharmaceutical and Cell-Based Therapies, 156-174 (Sadettin Ozturk and Wei-Shou Hu eds., Taylor and Francis Group 2006). In some cases, some level of agitation of the media and the suspended cells is necessary. Agitation may be minimized to avoid denaturation of media components and shearing of the cells during cultivation.

The cell seeding densities for each experimental condition can be optimized for the specific culture conditions being used. For routine monolayer culture in plastic culture vessels, an initial seeding density of $1\text{-}5 \times 10^5$ cells/cm$^2$ may be preferable, while for suspension cultivation, a higher seeding density (e. g., $5\text{-}20 \times 10^5$ cells/ml) may be used.

Mammalian cells are typically cultivated in a cell incubator, preferably at about 37° C., but it could be anywhere between 30° C. to 39° C. Non-mammalian cells may have other preferred temperatures for cultivation. Cultivation of mammalian and non-mammalian cells can be done in steps, for instance, at one temperature for optimal cell growth, and at another temperature for optimal protein/peptide/fragment or virus production. The incubator atmosphere may be humidified and may contain about 3-10% carbon dioxide in air, more preferably about 5-10% carbon dioxide in air, and most preferably about 3-8% carbon dioxide in air, although cultivation of certain cell lines may require as much as 20% carbon dioxide in air for optimal results. Culture medium pH may be in a preferred range depending on the cell type, for example of about 6-8.5, preferably about 7.1 to 7.6, or preferably about 7.1 to 7.4, or more preferably about 7.1 to 7.3 or preferably about 6-6.3 for insect cells.

Cells in closed or batch culture should undergo complete medium exchange (i. e., replacing spent media with fresh media) when the cells reach a density of about $1.5\text{-}2.0 \times 10^6$ cells/ml. Cells in perfusion culture (e. g., in bioreactors or fermenters) will receive fresh media on a continuously recirculating basis.

8. Virus Production

In addition to cultivation of cells in suspension or in monolayer cultures, the present media may be used in methods for producing viruses from mammalian cells. Such methods comprise (a) contacting a cell (e.g., a mammalian cell) with a virus under conditions suitable to promote the infection of the cell by the virus; and (b) cultivating the cell in the small peptide- or dipeptide-containing cell culture media described herein under conditions suitable to promote the production of virus by the cell. The cell may be contacted with the virus either prior to, during or following cultivation of the cell in the culture media. Optimal methods for infecting a mammalian cell with a virus are well-known in the art and will be familiar to one of ordinary skill. Virus-infected mammalian cells cultivated in the culture media described herein may be expected to produce higher virus titers (e. g., 2-, 3-, 5-, 10-, 20-, 25-, 50-, 100-, 250-, 500-, or 1000-fold higher titers) than cells cultivated in a cell culture media other than the cell culture media described herein.

These methods may be used to produce a variety of mammalian viruses or viruses adapted to infect mammalian cells, viral like particles and viral vectors, including but not limited to adenoviruses and derivatives thereof, adeno-associated viruses and derivatives thereof, retroviruses and derivatives thereof, lentiviruses and derivatives thereof, insect viruses like baculoviruses and derivatives thereof, sendai virus and derivatives thereof, and so on. Following cultivation of the infected cells in the culture media described herein, the used culture media comprising viruses, which may be a recombinant virus, viral vectors, viral particles or components thereof (proteins and/or nucleic acids (DNA and/or RNA)) may be used for a variety of purposes, including vaccine production, production of inhibitory RNA molecules like miRNA, siRNA, etc., production of viral vectors for use in cell transfection or gene therapy, infection of animals or cell cultures, study of viral proteins and/or nucleic acids and the like. Alternatively, viruses, viral vectors, viral particles or components thereof may optionally be isolated from the used culture medium according to techniques for protein and/or nucleic acid isolation that will be familiar to one of ordinary skill in the art.

In one embodiment, the cells produce VLPs. "VLPs" or "virus-like particles" are vehicles for delivering one or more compounds, including biological materials such as lipids, carbohydrates, proteins and nucleic acids into cells. Other compounds which may be delivered with VLPs include dyes (e.g., fluorescent dyes), labels (e.g., fluorescent or radioactive labels), and drugs (e.g., antibiotics or anti-viral agents). VLPs generally contain at least one viral protein. Typically, a viral protein surrounds the compounds. However, in particular instances, compounds to be delivered can be associated with a VLP by means other than by inclusion in the VLP. For example, compounds may be attached (e.g., covalently or non-covalently attached) to a viral protein, or can be integrated into the envelope, when present. In one aspect, VLPs may be associated with various types of nucleic acids (e.g., heterologous nucleic acids) such as DNA, RNA, both RNA and DNA, or RNA/DNA hybrids, or derivatives known in the art. Examples of VLPs include viral particle products produced by using VIRAPOWER™ adenoviral and lentiviral vector kits (see, e.g., Invitrogen Corporation, cat. nos. K4930-00, K4940-00, K4950-00, K4955-00, K4960-00, K4965-00, K4967-00, and K4985-00).

Viruses which may be used to prepare VLPs include, for examples, phage, (e.g., T even phages (e.g., T4 phage, etc.), T odd phage (e.g., T7 phage, etc.), bacteriophage phi29, lambda phage, etc.), baculoviruses, adenoviruses, adeno-associated viruses, lentiviruses (e.g., Moloney Murine leukemia virus, HIV1, HTLV-III, etc.), sendai viruses, pox viruses, and alphaviruses (e.g., Semliki Forest Virus, SindBis Virus, etc.). Additional examples of viruses which may be used to prepare VLPs, as well as methods for preparing VLPs are described elsewhere herein.

9. Recombinant Protein Production

The present culture media may also be used in methods for the production of recombinant proteins from cells described above, preferably mammalian cells, and particularly from mammalian cells grown in suspension. Because the present culture media provide for rapid, high-density suspension cultivation of mammalian cells, the present methods facilitate enhanced production of recombinant proteins. By protein is meant, either, a full-length protein, a protein fragment, a peptide, a cleaved protein product, a cross-linked protein product, tagged-peptide or proteins, etc. By protein is also meant all types of natural and altered proteins, including recombinant, mutant, engineered, chimeric, glycoproteins, lipoproteins, active, processed proteins, etc. The protein may be naturally expressed by the cell or cell line, or the cell line may be engineered to express it using standard genetic engineering methods known in the art including, but not limited to, transfection, transduction, electroporation, etc. The resulting protein or peptide may be purified or isolated to a desired level of purity. The proteins or peptides or their fragments, that can be produced or expressed using the media and/or feed compositions of the invention include, but are not limited to, extracellular proteins, like laminins, fibronectin, integrins, etc., enzymes like caspases, proteases, subtilisin, kinases, RNAses, DNAses, etc., peptide hormones like insulin, PTHrP, etc., intracellular proteins including membrane proteins, receptors, nuclear proteins, endoplasmic reticular proteins, etc., antibodies, any antibody fragments like heavy- or light chains of the antibody, an antigen binding site or motif, a chimeric antibody etc. A chimeric antibody may be a species/species chimera or a class/class chimera. The expressed protein or polypeptide that may be produced using the compositions and media/feeds of the invention may be a human or mammalian derived protein sequence that is expressed in a non-animal cell line, like a plant cell, in order to produce animal origin-free proteins that are free of adventitious agents for downstream use in therapeutics.

Methods of producing a polypeptide according to the invention comprise cultivating a cell (e.g., a mammalian cell) that has been genetically engineered to produce a polypeptide in the small peptide- or dipeptide-containing cell culture media described herein under conditions suitable for expression of the polypeptide by the cell. Optimal methods for genetically engineering a mammalian cell to express a polypeptide of interest are well-known in the art and will therefore be familiar to one of ordinary skill. See e.g., Cell Culture Technology for Pharmaceutical and Cell-Based Therapies, 15-40 (Sadettin Ozturk and Wei-Shou Hu eds., Taylor and Francis Group 2006). Cells may be genetically engineered prior to cultivation in the media of the invention, or they may be transfected with one or more exogenous nucleic acid molecules after being placed into culture in the media. Genetically engineered cells may be cultivated in the present culture media either as monolayer cultures, or more preferably as suspension cultures according to the methods described above. Following cultivation of the cells, the polypeptide of interest may optionally be purified from the cells and/or the used culture medium according to techniques of protein isolation that will be familiar to one of ordinary skill in the art.

10. Detecting Small Peptides in Culture Media or in Concentrated Feeds

The small peptides and dipeptides described herein can be detected using any technique known in the art for detecting amino acids and/or small peptides, including but not limited to, acid hydrolysis, liquid chromatography, capillary electrophoresis (Brown et al., J. Chrom. (1994) A, 661: 279-285), HPLC (van Wandelen et al., J. Chrom. (1997) A, 763: 11-22), or mass spectrometry. Acid hydrolysis of peptides for chromatographic analysis of amino acid compositions and concentration is well-known in the art. Comparison of the chromatographic profiles of the amino acid peaks before and after acid hydrolysis can indicate the composition and concentration of amino acids, and therefore small peptides in a media, feed or supplement. For instance, if tyrosine were present in a small peptide in a media, its concentration would increase in the acid hydrolysate of the media sample (for e.g., the tyrosine peak height and/or area of the peak) compared to the peak height/area of the identical media sample before acid hydrolysis.

Figure 2:
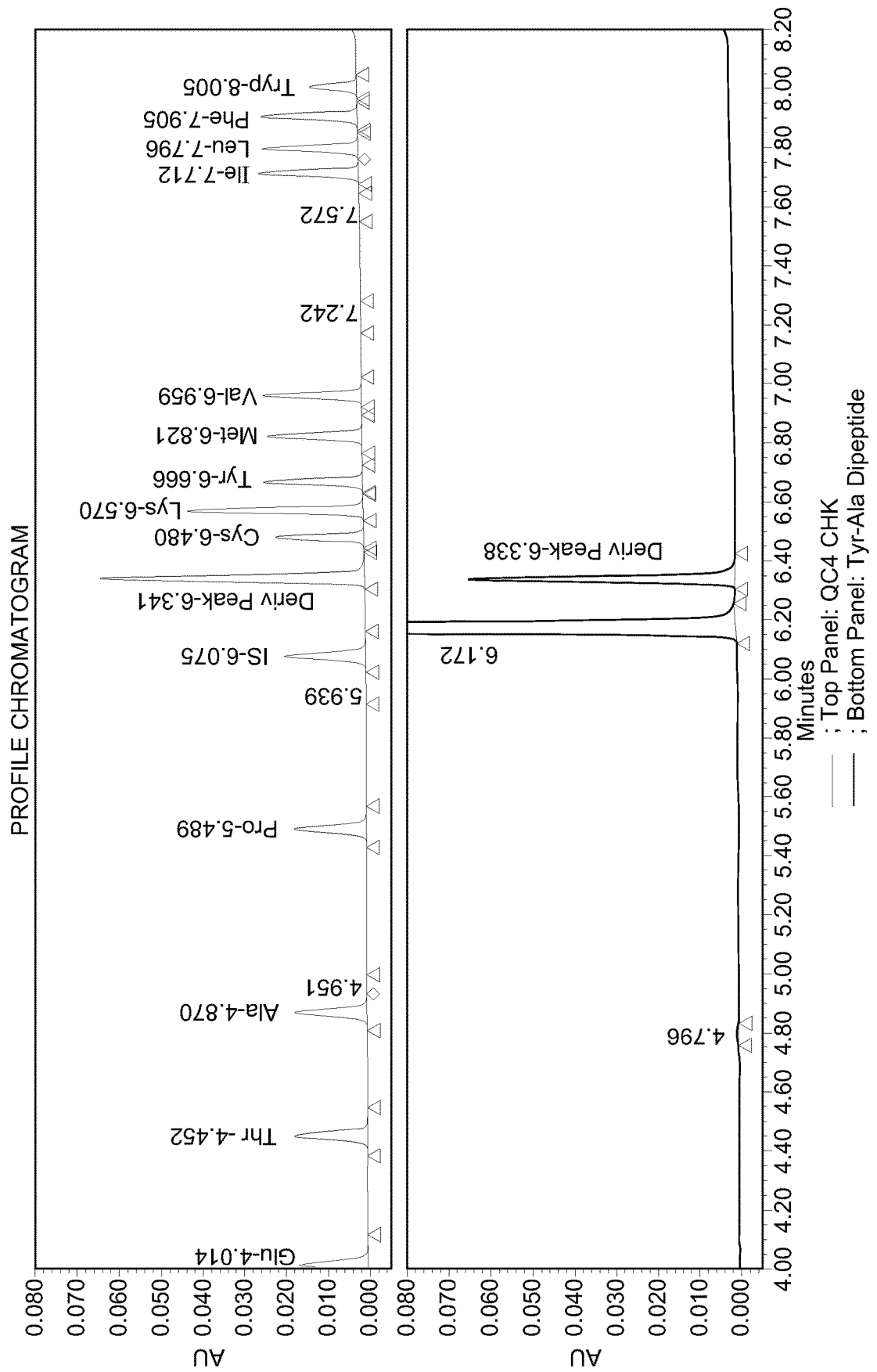
FIG. 2 shows an exemplary profile chromatogram of a solution containing the Ala-Tyr dipeptide, with the Ala-Tyr dipeptide represented by the peak at 6.172 minutes (bottom panel).
Figure 3:
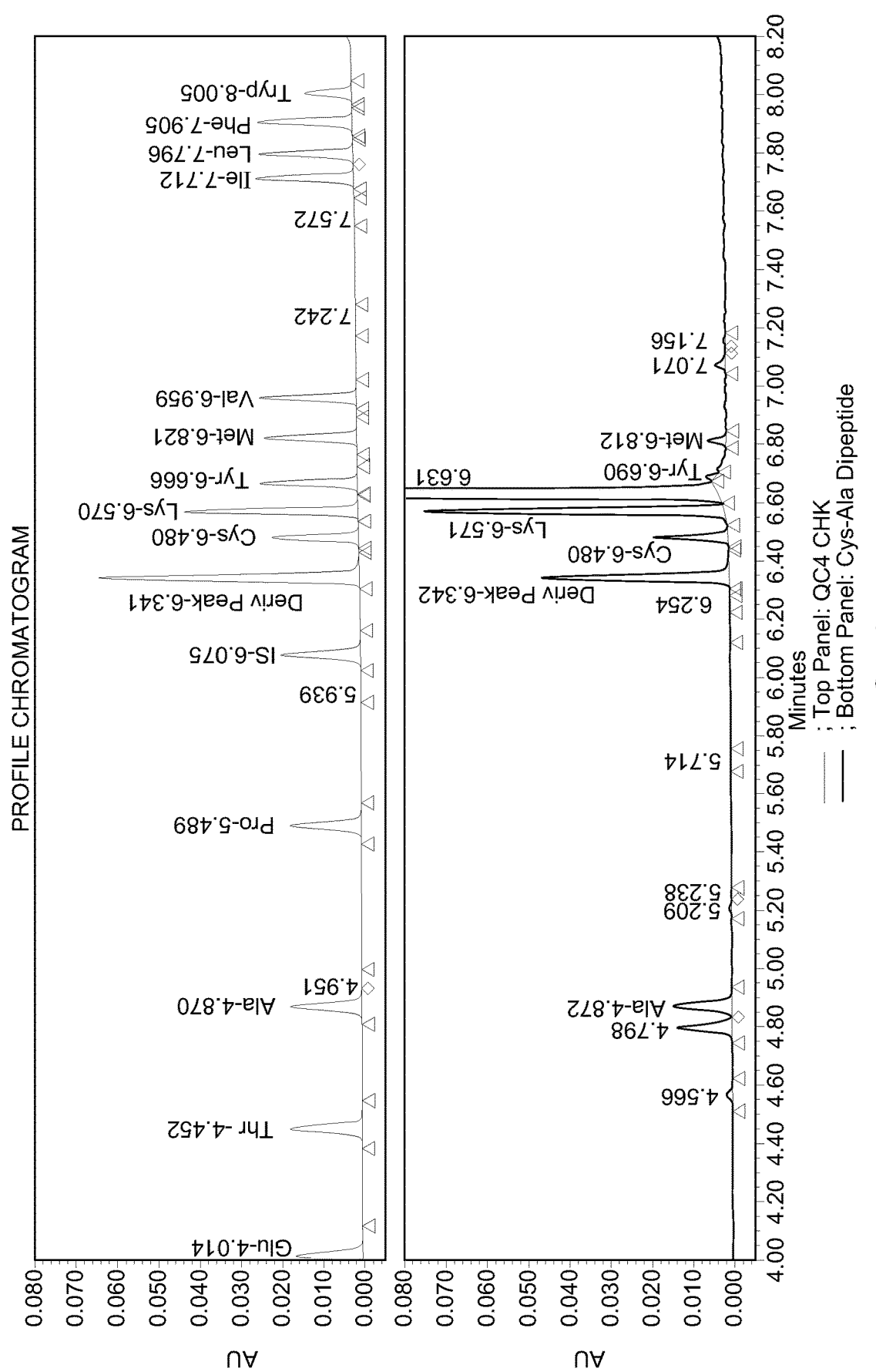
FIG. 3 shows an exemplary profile chromatogram of a solution containing the Ala-Cys dipeptide, with the Ala-Cys dipeptide represented by the peak at 6.631 minutes (bottom panel).
Figure 4:
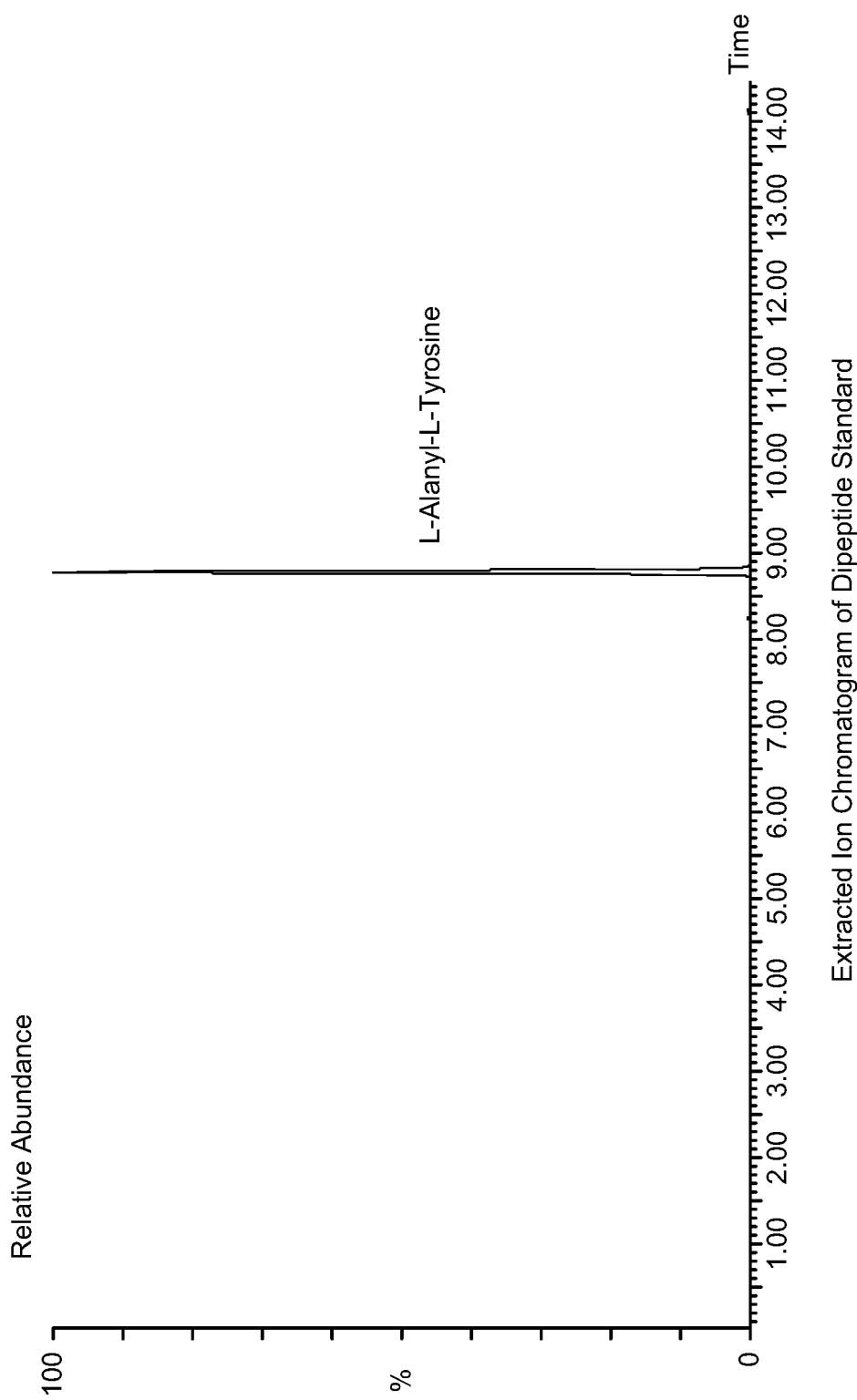
FIG. 4 shows an exemplary profile extracted ion chromatogram of a solution containing an Ala-Tyr dipeptide standard, represented by the peak at 8.8 minutes.
Figure 5:
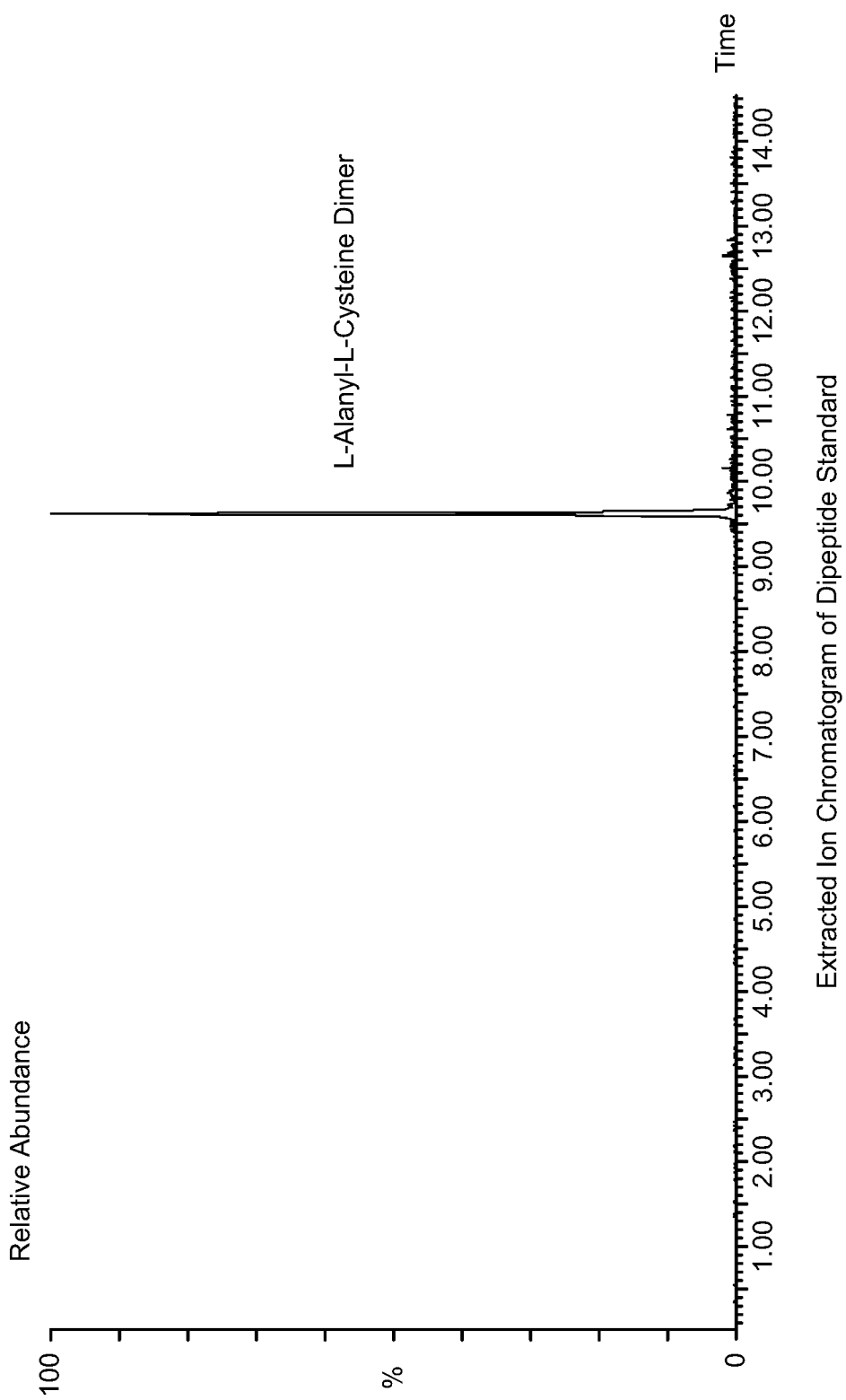
FIG. 5 shows an exemplary profile extracted ion chromatogram of a solution containing an Ala-Cys dimer standard, represented by the peak at 9.6 minutes.
Figure 6:
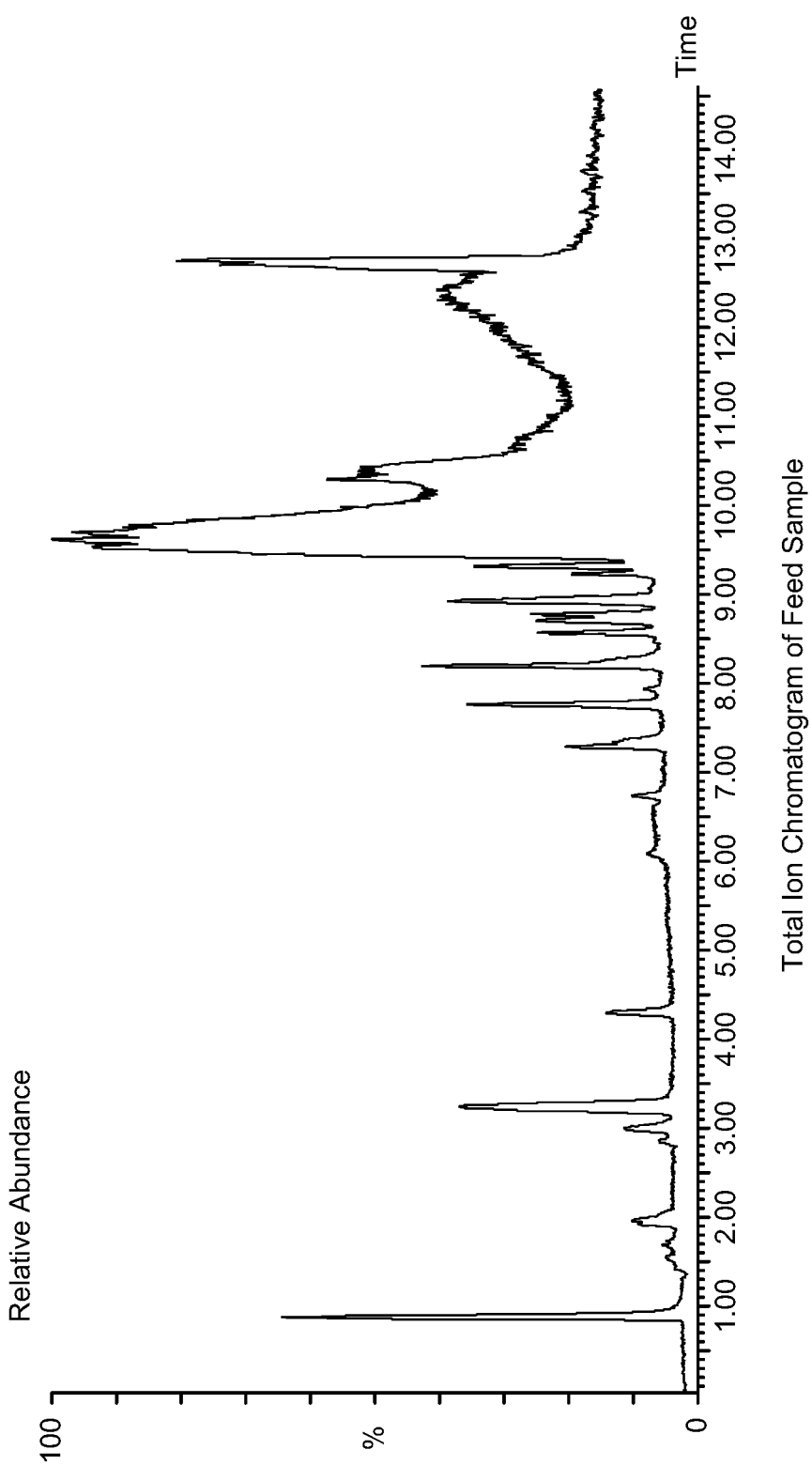
FIG. 6 shows an exemplary profile total ion chromatogram of an exemplary feed sample containing an Ala-Cys dimer and an Ala-Tyr dipeptide.
Figure 7:
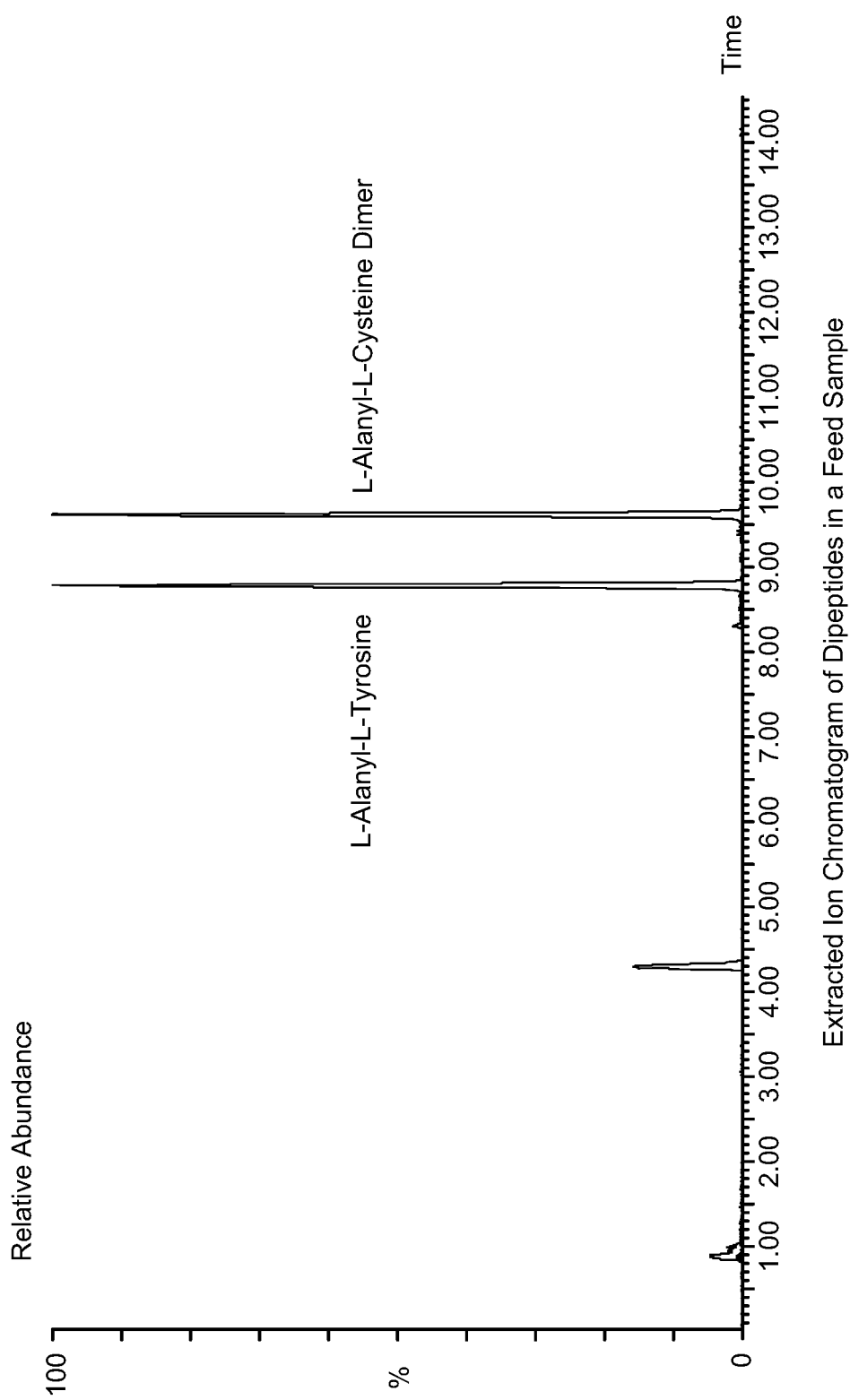
FIG. 7 shows an exemplary profile extracted ion chromatogram of an exemplary feed sample containing an Ala-Tyr dipeptide and an Ala-Cys dimer.

By way of example, the alanyl tyrosine and alanyl cysteine dipeptides described herein were detected using the methodology described in van Wandelen et al., J. Chrom. (1997) A, 763: 11-22, which involved the HPLC (High Performance Liquid Chromatograph) separation of 6-aminoquinolyl-N-hydroxysuccinimidyl carbamate (AQC)-derivatized amino acid mixtures on an AccQ-Tag Ultra™ (Waters Corp., Milford, Mass.) column (2.1×100 mm, 1.7 μm). The detector parameters were set as follows: wavelength mode: single wavelength; wavelength: 260 nm; sampling rate: 20 (points/sec); time constant: 0.4000 (sec). Using these parameters, in an exemplary run, a sample of the alanyl tyrosine dipeptide had a peak elution time of about 6.172 minutes (see FIG. 2), immediately after the internal standard (AABA), and in another exemplary run, a sample of the alanyl cysteine dipeptide had a peak elution rate of 6.631 minutes, between lysine and tyrosine (see FIG. 3).

This AccQ-Tag™ Ultra (Waters Corp., Milford, Mass.) Pre-Column Derivatization with Ultra High Performance Liquid Chromatograph (UPLC) method, thus, provides one way to test any sample media or feed supplement to see if it contains a small peptide comprising cysteine or tyrosine, for instance the dipeptides, alanyl tyrosine or alanyl cysteine. The same method could also be used to detect other small peptides, including other dipeptides of interest.

In addition, the dipeptides described herein can also be quantified with liquid chromatography with mass spectrometry detection (LC/MS). Separation was performed with reverse phase liquid chromatography column (Acquity UPLC® HSS T3 1.8-μm, 2.1-mm i.d×150-mm at 40° C.) coupled to a quadruple time-of-flight mass spectrometer (Waters® SYNAPT™ HDMS™ System, Milford, Mass.). Perfluorinated carboxylic acid (for e.g., perfluoropentanoic acid) was used as the ion pairing agent for optimum separation of polar compounds (Jun Qu, Yiming Wang, Guan Luo, Zhuping Wu, and Chengdui Yang, Anal. Chem., 2002, 74, 2034-2040; hereby incorporated by reference in its entirety). Mobile phase-A was 0.1% formic acid and 0.05% perfluoropentanoic acid in water, and mobile phase-B was 0.1% formic acid and 0.05% perfluoropentanoic acid in 80% acetonitrile. All reagents were LC/MS grade. Ultra-performance liquid chromatography (UPLC) gradient was linear over 1-45% of mobile phase-B with a 0.4-mL/min flow rate for 15 min. Mass spectra was collected every 0.5-sec within 70-1000 Da in continuum, positive electrospray (+ES), and V-mode. Protonated L-alanyl-L-cysteine dimer and protonated L-alanyl-L-tyrosine ions were extracted from total ion chromatograms as 383.105 (±0.03) Da and 253.118 (±0.03) Da, respectively. Retention times for protonated L-alanyl-L-cysteine dimer and protonated L-alanyl-L-tyrosine ions were 9.60 (±0.03) min and 8.75 (±0.03) min, respectively (FIGS. 4 to 7).

Unless otherwise defined, all technical and scientific terms used herein have the same meaning as commonly understood by one of ordinary skill in the art. In case of conflict, the present specification, including definitions, will control. It will be readily apparent to one of ordinary skill in the relevant arts that other suitable modifications and adaptations to the methods and applications described herein are obvious and may be made without departing from the scope of the invention or any embodiment thereof. In addition, the materials, methods, and examples are illustrative only and not intended to be limiting. All publications, patent applications, patents, and other references mentioned herein are incorporated by reference in their entirety.

Example 1: Production of Dipeptide-Containing Culture Medium

An exemplary cell culture medium containing the dipeptides alanyl tyrosine (AlaTyr) and alanyl cysteine (which forms a disulfide dimer, [AlaCys]2) was prepared. Specifically, the dipeptides, alanyl tyrosine and alanyl cysteine were added as dry powder to an aqueous basal cell culture medium containing glucose and a mixture of concentrated amino acids and mixed until dissolved. Alanyl tyrosine was added to the cell culture medium at a concentration of about 4.0 g/L. Alanyl cysteine was added to the cell culture medium at a concentration of about 3.0 g/L. The observed solubilities of the dipeptides in water were determined to be about 15.4 g/L for AlaTyr, >100 g/L for AlaCys, and about 8.7 g/L for [AlaCys]2 dimer. By way of comparison, the solubility of L-Tyrosine in water is about 0.38 g/L at 20° C. Free L-Cysteine is easily oxidized into cystine. L-Cysteine hydrochloride is considerably more stable in an acidic aqueous solution, but in neutral or alkaline aqueous solutions, it is also converted to L-Cystine by aerobic oxidation. The solubility of L-Cystine in water was about 0.11 g/L at 25° C.

Example 2: Fed Batch Testing

Integrated fed batch testing was performed using IgG-producing CHO cells grown in a basal cell culture medium CD FortiCHO™ (Invitrogen Cat. No. A-1148301 and Custom Stock A-11437DK; Life Technologies Corp., Carlsbad, Calif.) and supplemented with either glucose (CD FortiCHO™+Glucose; FIG. 1: curve with filled squares (—■—) and forward slash-filled bar (▨) or, with a mixture of concentrated amino acid mixture with low levels of cysteine or tyrosine, with glucose+the dipeptide (DP) containing culture medium or feed, described in Example 1 (CD FortiCHO™+aa+DP Feed FP2 and FP3; see FIG. 1: (FP2) curve with filled circles (—●—) and unfilled bar (☐); (FP3) curve with filled diamonds (—♦—) and backward slash-filled bar (▧). "aa" in FIG. 1 refers to a mixture of concentrated amino acid mixture with low levels of cysteine and tyrosine, with glucose.

Other basal cell culture media studied were either CD OptiCHO™, CD CHO; all from Life Technologies Corp., Carlsbad, Calif. (data not shown). The preferred medium used was CD FortiCHO™. Exemplary mixtures of concentrated amino acids are, for instance, CHO CD EfficientFeed™ A (Invitrogen Cat. No. A1023401), CHO CD EfficientFeed™ B (Invitrogen Cat. No. A1024001), CHO CD Efficient Feed™ kit (Invitrogen Cat. No. A1024101), CD Efficient Feed™ C AGT™ (Custom Stock A-11525SA, Life Technologies Corp., Carlsbad, Calif.). The cysteine and tyrosine containing small peptides in the cell culture media or supplemental feeds of the invention are designed to be used with any exemplary basal cell culture medium, with any exemplary, stoichiometrically-balanced, mixture of concentrated amino acids (aa) optionally with glucose, vitamins, trace elements, etc., suitable for the growth of a desired cell type, as can be deemed by one skilled in the art.

The cells were grown in DasGip bioreactors with 500 mL working volume, with a pH control set point of 7.0+/−0.05 and a pO2 control set point of 30%. CHO cells supplemented with glucose were automatically fed 3 g/L of glucose whenever the glucose level reached 2 g/L. CHO cells supplemented with dipeptides (DP) were subjected to two feeding schedules. In the first feeding schedule (see FIG. 1, red curve and bar: FP2), CHO cells were fed 2% of the dipeptide-containing medium daily from day 4 to day 13. In the second schedule, (see FIG. 1, green curve and bar: FP3), CHO cells were fed 2% of the dipeptide-containing medium daily from day 5 to day 14.

Cells grown in CD FortiCHO™ medium and supplemented with glucose had comparable or better IgG productivity (1600 mg/L) than CD Opti CHO™ (Life Technologies, Corp., Carlsbad, Calif.) or CD CHO (Life Technologies, Corp., Carlsbad, Calif. Carlsbad, Calif.) based fed-batch processes (data not shown). CHO cells grown in CD FortiCHO™ and supplemented with the concentrated amino acids and the dipeptide-containing medium of Example 1 had improved viability after 12 days and doubled productivity levels, with an IgG titer of about 3200 mg/L by day 15, as compared to an IgG titer of about 1600 mg/L for CD FortiCHO™+Glucose at day 15 (FIG. 1). Of the two feeding schedules for CD FortiCHO™+aa+Dipeptide (DP) Feed, both worked well and showed comparable levels of IgG production. The FP3 profile had a better maintained glucose level and a more constant level of IgG production than FP2, while the FP2 profile promoted a higher peak cell density. Notably, the dipeptide-containing cell culture medium yielded enhanced cell density and productivity levels at a significantly reduced volumetric feed proportion, providing yet another advantage of using the dipeptide-containing cell culture medium described herein.

A liquid cell culture medium or feed solution containing the dipeptides alanyl tyrosine and alanyl cysteine can be stored at 2-8° C., has remained precipitate free for over 10 months, thus demonstrating significantly longer liquid stability than expected for such a concentrated solution.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed:

1. A cell culture supplement, concentrated feed, or cell culture medium comprising an alanine-cysteine dipeptide and an alanine-tyrosine dipeptide, wherein the cell culture supplement is a dry powder, wherein the cell culture medium further comprises a carbohydrate and a mixture of amino acids, and wherein the cell is a mammalian cell.

2. The cell culture medium of claim 1, wherein the carbohydrate is a hexose and the amino acids are concentrated.

3. The cell culture medium of claim 2, wherein the hexose is a glucose.

4. The cell culture supplement of claim 1, wherein the dry powder is an agglomerated powder (AGT), a dry powder media (DPM), or an advanced powder media (APM).

5. The cell culture supplement of claim 4, wherein a solvent can be added to the dry powder to make a liquid.

6. The cell culture supplement of claim 5, wherein the solvent is water.

7. The cell culture supplement of claim 1, wherein the liquid can be added directly to a cell culture.

8. The cell culture supplement, concentrated feed, or cell culture medium of claim 1, wherein the cell culture supplement, concentrated feed, or cell culture medium increases the titer of a recombinant protein produced in a mammalian cell.

9. The cell culture supplement, concentrated feed, or cell culture medium of claim 1, wherein the alanine-cysteine dipeptide and alanine-tyrosine dipeptide each are present at a concentration of about 1 g/L to about 16 g/L.

10. The cell culture supplement, concentrated feed, or cell culture medium of claim 1, wherein the alanine-cysteine dipeptide and alanine-tyrosine dipeptide each are present at a concentration of about 2.5 g/L to about 8.5 g/L.

11. The cell culture supplement, concentrated feed, or cell culture medium of claim 1, wherein the alanine-cysteine dipeptide can be bonded to another alanine-cysteine dipeptide by a disulfide linkage.

12. The cell culture supplement, concentrated feed, or cell culture medium of claim 11, wherein the disulfide linkage is the result of an oxidation reaction in which two cysteine residues are linked together by a disulfide bond to form cystine $(SCH_2CH(NH_2)CO_2H)_2$.

* * * * *